United States Patent
Alving et al.

(10) Patent No.: US 11,796,546 B2
(45) Date of Patent: Oct. 24, 2023

(54) METHODS FOR QUANTIFYING DRUG CONCENTRATION IN A PRODRUG COMPOSITION

(71) Applicant: GENZYME CORPORATION, Cambridge, NJ (US)

(72) Inventors: Kim Alving, Waltham, MA (US); Bing Wang, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 841 days.

(21) Appl. No.: 16/867,655

(22) Filed: May 6, 2020

(65) Prior Publication Data
US 2020/0386768 A1 Dec. 10, 2020

Related U.S. Application Data

(60) Provisional application No. 62/844,579, filed on May 7, 2019.

(51) Int. Cl.
*G01N 33/68* (2006.01)
*A61K 47/61* (2017.01)

(52) U.S. Cl.
CPC .......... *G01N 33/6848* (2013.01); *A61K 47/61* (2017.08); *G01N 2333/926* (2013.01); *G01N 2333/96486* (2013.01); *G01N 2333/988* (2013.01)

(58) Field of Classification Search
CPC .......... G01N 33/6848; G01N 33/6851; G01N 33/15; A61K 47/61
See application file for complete search history.

(56) References Cited

U.S. PATENT DOCUMENTS

2018/0289822 A1* 10/2018 Kadereit ............ A61K 47/6903
2020/0108153 A1* 4/2020 Adams .................. A61K 47/10

OTHER PUBLICATIONS

Baker, A.E.G. et al. "Independently Tuning the Biochemical and Mechanical Properties of 3D Hyaluronan-Based Hydrogels with Oxime and Diels-Alder Chemistry to Culture Breast Cancer Spheroids," Biomacromolecules 2017, 18, 12, 4373-4384 (Year: 2017).*
Ågerup et al., "Non-animal stabilized hyaluronic acid: a new formulation for the treatment of osteoarthritis", BioDrugs, 2005, vol. 19, No. 1, pp. 23-30.
Dharanipragada, "New modalities in conformationally constrained peptides for potency, selectivity and cell permeation", Future Medicinal Chemistry, 2013, vol. 5, No. 7, p. 831.

(Continued)

*Primary Examiner* — Jennifer Wecker
*Assistant Examiner* — Michelle Adams
(74) *Attorney, Agent, or Firm* — LATHROP GPM LLP; James H. Velema; Judith L. Stone-Hulslander

(57) ABSTRACT

Methods for quantifying the amount of drug present in a crosslinked hyaluronic acid-linker-peptide (xHA-L-P) prodrug composition are provided. Disclosed are steps of contacting a sample of the xHA-L-P prodrug formulation with a hyaluronoglucosidase to generate oligomeric hyaluronic acid-linker-peptide drug (oHA-L-P), contacting the oHA-L-P with a second enzyme to generate peptide digest products of the drug, and detecting the peptide digest products to determine the amount of the drug present in the xHA-L-P prodrug formulation.

20 Claims, 21 Drawing Sheets

Specification includes a Sequence Listing.

(56) References Cited

OTHER PUBLICATIONS

Edsberg et al., "Intra-articular Duration of Durolane™ after Single Injection into the Rabbit Knee", Cartilage, 2011, vol. 2, No. 4, pp. 384-388.
Fang et al., "Temperature-sensitive hydrogels composed of chitosan and hyaluronic acid as injectable carriers for drug delivery", Eur J Pharm Biopharm, 2008, vol. 68, No. 3, pp. 626-636.
Gupta et al., "Fast-gelling injectable blend of hyaluronan and methylcellulose for intrathecal, localized delivery to the injured spinal cord", Biomaterials, 2006, vol. 27, No. 11, pp. 2370-2379.
Ha et al., "Preparation of thermo-responsive and injectable hydrogels based on hyaluronic acid and poly(N-isopropylacrylamide) and their drug release behaviors", Macromolecular Research, 2006, vol. 14, No. 1, pp. 87-93.
Hoare et al., "Hydrogels in drug delivery: progress and challenges", Polymer, 2008, vol. 49, No. 8, pp. 1993-2007.
Kaspar et al., "Future directions for peptide therapeutics Development", Drug Discovery Today, 2013, vol. 18, pp. 807-817.
Kenne et al., "Modification and cross-linking parameters in hyaluronic acidhydrogels—Definitions and analytical methods", Carbohydrate Polymers 2013, vol. 91, pp. 410-418.
Khunmanee et al., "Crosslinking method of hyaluronic-based hydrogel for biomedical applications", J. Tissue Engineering, 2017, vol. 8, pp. 1-16.
La Gatta et al., "Comparative anaiysis of commercial dermal filters based on crosslinked hyaluronan: Physical characterization and in vitro enzymatic degradation", Polymer Degradatian and Stability, 2011, vol. 96, Issue 4, pp. 630-636.
Lau et al., "Therapeutic peptides: Historical perspectives, current development trends, and future directions", Bioorganic & Medicinal Chemistry, 2018, vol. 26, Issue 10, pp. 2700-2707.
Martin et al., "Selection of Dissolution Medium for QC Testing of Drug Products", Journal of Validation Technology, Summer 2011, pp. 7-11.
Nagaoka et al., "Regulation of Hyaluronan (HA) Metabolism Mediated by HYBID (Hyaluronan-binding Protein Involved in HA Depolymerization, KIAA1199) and HA Synthases in Growth Factor-stimulated Fibroblasts", 2015, vol. 290, No. 52, pages.
Stern et al., "Carbohydrate Polymers at the Center of Life's Origins: The Importance of Molecular Processivity", Chem. Review, 2008, vol. 308, No. 12, pp. 5061-5085.
Stern et al., "The Hyaluronidases: Their Genomics, Structures, and Mechanisms of Action", Chem. Rev., 2006, vol. 106, No. 3, pp. 818-839.
Stern et al., "The many ways to cleave hyaluronan" Biotechnology Advances, 2007, vol. 25, pp. 537-557.
Tillner et al., "A novel dual glucagon-like peptide and glucagon receptor agonist SAR425899: Results of randomized, placebo-controlled first-in-human and first-in-patient trials", Diabetes Obes. Metab., 2019, vol. 21, No. 1, p. 120.
Yamaguchi et al., "TMEM2: A missing link in hyaluronan catabolism identified?", Matrix Biol., May 2019, vol. 78-79, pp. 139-146.
Yoshida et al., "KIAA1199, A deafness gene of unknown function, is a new hyaluronan binding protein involved in hyaluronan depolymerization", Proc. Natl. Acad. Sci. U.S.A., 2013, vol. 110, No. 14, pp. 5612-5617.
Yoshino et al., "The role and regulation of TMEM2 (transmembrane protein 2) in HYBID (hyaluronan (HA)-binding protein involved in HA depolymerization/KIAA1199/CEMIP)-mediated HA depolymerization in human skin fibroblasts", Biochemical and Biophysical Research Communications, 2018, vol. 505, Issue 1, pp. 74-80.
Ding et al., "pH-Sensitive Coiled-Coil Peptide-Cross-Linked Hyaluronic Acid Nanogels: Synthesis and Targeted Intracellular Protein Delivery to CD44 Positive Cancer Cells", Biomacromolecules, Jan. 12, 2018, 19(2): p. 555-562.
International Preliminary Report on Patentability for PCT International Patent Application No. PCT/US2020/031605, dated Nov. 2, 2021.
International Search Report and Written Opinion for PCT International Patent Application No. PCT/US2020/031605, dated Aug. 26, 2020.
Yang et al., "Molecular design of hyaluronic acid hydrogel networks for long-term controlled delivery of human growth hormone", Soft Matter, Jan. 2011, 7(3): 868.
Yang et al., "Target specific hyaluronic acid interferon alpha conjugate for the treatment of hepatitis C virus infection", Biomaterials, Jul. 30, 2011, 32(33): 8722-8729.

\* cited by examiner

| Conc (ug/mL) | Curve in buffer | Curve in matrix |
|---|---|---|
| 0.01 | 2.42E+06 | 2.64E+06 |
| 0.02 | 3.58E+06 | 3.98E+06 |
| 0.04 | 6.01E+06 | 6.30E+06 |
| 0.08 | 1.04E+07 | 1.16E+07 |
| 0.16 | 2.04E+07 | 2.11E+07 |
| 0.31 | 3.95E+07 | 4.00E+07 |
| 0.63 | 7.95E+07 | 7.54E+07 |
| 1.25 | 1.55E+08 | 1.50E+08 |
| 2.50 | 3.20E+08 | 3.07E+08 |
| 5.00 | 6.37E+08 | 6.20E+08 |

| | |
|---|---|
| IS | 7.06E+08 |
| IS | 7.16E+08 |
| IS | 7.13E+08 |
| IS | 7.52E+08 |
| IS | 7.32E+08 |
| IS | 7.36E+08 |
| IS | 7.24E+08 |
| IS | 7.12E+08 |
| IS | 7.27E+08 |
| IS | 7.21E+08 |
| IS | 7.47E+08 |
| IS | 7.49E+08 |
| IS | 7.36E+08 |
| IS | 7.56E+08 |
| IS | 7.55E+08 |
| IS | 7.37E+08 |
| IS | 7.28E+08 |
| IS | 7.39E+08 |
| IS | 7.33E+08 |
| IS | 7.24E+08 |
| IS | 7.49E+08 |
| Average | 7.33E+08 |
| Stdev | 1.48E+07 |
| CV | 2.02 |

| Measured ug/mL | Conc. Corrected for total dilution | % peptide |
|---|---|---|
| 0.62 | 194.0 | 19.4 |
| 0.54 | 167.6 | 16.8 |
| 0.59 | 185.2 | 18.5 |
| | average | 1.8E+01 |
| | stdev | 1.3E+00 |
| | %CV | 7.4E-02 |

METHODS FOR QUANTIFYING DRUG CONCENTRATION IN A PRODRUG COMPOSITION

RELATED APPLICATION

This application claims priority to U.S. Provisional Patent Application Ser. No. 62/844,579, filed May 7, 2019, the entire disclosure of which is hereby incorporated herein by reference in its entirety.

FIELD OF THE INVENTION

The present invention relates to methods for quantifying the amount of drug present in a prodrug composition.

BACKGROUND

On average over the past decade, 17 new peptides have entered clinical trials every year with approval rates (from phase 1 to marketing) of twice that of small molecules (Dharanipragada (2013) Future Medicinal Chemistry 5(7): 831; Kaspar and Reichert (2013) Drug Discovery Today 18:807-817), and more than 150 peptide drug candidates are currently in development (Lau and Dunn (2018) Bioorganic & Medicinal Chemistry 26:2700-2707).

The development of peptide drugs presents specific challenges, however. For example, peptide drugs are subject to proteolytic cleavage and are cleared quickly in vivo. Oral delivery remains challenging, in part due to low permeability of biological membranes. Attempts to remedy these shortcomings have been made by incorporating conformational constraints such as cyclic peptide formation (e.g., by lactamizations and click-cyclizations), hydrocarbon stapling, lipidation, and the development of polymer drug conjugates.

One example of a peptide drug is SAR425899, a dual receptor agonist that targets the glucagon and GLP1 receptors and can facilitate glycemic control and weight loss in type 2 diabetes mellitus patients, as well as weight loss in healthy volunteers (Tillner et al. (2019) Diabetes Obes. Metab. 21:120, doi: 10.1111/dom.13494, Epub 2018 Sep. 16). However, due to rapid in vivo clearance, a once daily dose of SAR425899 is required.

Hyaluronic acid (HA), also referred to as hyaluronan, is a naturally occurring non-sulfate linear polysaccharide composed of repeating disaccharide units of d-glucuronic acid and N-acetyl-d-glucosamine linked by β-1-3 and β-1-4 glycosidic bonds (Khunmanee et al. (2017) *J. Tissue Engineering vol.* 8 (doi: doi.org/10.1177/2041731417726464)). HA is an important structural element in the skin and participates in a number of cell surface receptor interactions. HA has immunosuppressive and antiangiogenic activity, and is present in brain tissue, hyaline cartilage, and synovial joint fluid. Due to its strong hydrophilic character and its high molecular weight in biological tissues that can absorb a large amount of water, up to 1000 times its solid volume, HA exhibits important structural and functional roles in the body.

Because of its biocompatibility and biodegradability, HA has found numerous applications in biomedical and pharmaceutical applications. However, HA is highly soluble and often exhibits very poor mechanical properties with rapid degradation behavior in vivo. Thus, HA has been chemically modified and/or crosslinked to improve its properties, including mechanical, viscosity, solubility, degradation, and biologic. HA derivatives have been created and utilized in scaffolds for tissue engineering, in soft tissue surgery such as vocal fold augmentation, drug delivery, intracellular delivery of siRNA, wound healing, and as a device in surgical procedures.

Crosslinked hyaluronic acid (xHA) forms a multi-million Dalton hydrogel in an aqueous environment, and can be linked to a drug (e.g., a peptide drug) to stabilize the drug in vivo. However, it is difficult to both quantify the amount of drug loaded in the hydrogel, and to quantify the release rate of the drug from the hydrogel. Simple UV measurements typically applied for basic quantification of peptides in solution cannot be applied for hydrogels, as such analyses require that the drug linked hydrogel complex be fully dissolved.

Alternative methods for accelerated hydrolysis of linker and release of a peptide drug using elevated temperature or elevated pH lead to partial degradation of the peptide drug, thus producing a heterogeneous mixture that is challenging to quantify. Accordingly, analytical quantification methods are needed to quantify drug loading of prodrug compositions on crosslinked HA hydrogels.

SUMMARY OF THE INVENTION

To address the analytical challenges of determining drug loading on a crosslinked HA (xHA) hydrogel, e.g., to enable peptide load determination of an xHA hydrogel, novel methods were discovered that permit accurate quantification of drug load (e.g., biopolymeric peptide prodrug load) measured as weight/weight percentage. The methods described herein are highly selective for drug load determination that can be applied to any small molecule (e.g., a polypeptide, a polynucleotide or the like) which can be broken down into smaller components (e.g., by proteolytic digestion, hydrolysis or the like), and can broadly be applied for drug load determination of prodrugs, e.g., biopolymer-containing prodrugs. The methods described herein are useful, for example, for controlling dose delivery of the drug in vivo, and for quality control of drug load among prodrug batches during manufacturing. The methods described herein enable the production of drugs, e.g., peptide drugs, that have increased half-lives in vivo, e.g., drugs such as peptide drugs having half-lives that are increased from minutes to days.

The methods described herein provide a variety of advantages over previous methods known in the art, such as NMR-based methods. For example, NMR-based methods take longer and have lower throughput than the methods described herein. NMR-based methods require milligrams of material, whereas the novel methods described herein require only nanograms of material. Furthermore, the dynamic range of NMR-based methods is lower than that of the novel methods described herein. In addition, NMR-based methods are more susceptible to interference by contaminating peptides than the novel methods described herein.

Novel methods are provided herein based on the discovery that a double enzymatic digestion followed by quantification of digestion product(s) can be used to accurately quantify drug load (e.g., peptide drug load) on a hydrogel. In certain embodiments of the method, a crosslinked hyaluronic acid-linker-peptide (xHA-L-P) is incubated with an enzyme to digest the crosslinked hyaluronic acid. Subsequently, a proteolytic enzyme is applied to digest the attached peptide and produce proteolytic digest products. The proteolytic digest products, which represent the peptide, are subsequently quantified.

In certain exemplary embodiments of the method, a crosslinked hyaluronic acid linker peptide conjugate (xHA-L-P) is weighed and suspended as a hydrogel in buffer. The hydrogel is enzymatically degraded to oligomeric hyaluronic acid-linker-peptide (oHA-L-P), which is soluble. The resulting oligomers of oHA-L-P are present as a heterogeneous mixture, consisting of peptide, linker and oligomeric hyaluronic acids of different lengths. This oligomeric hyaluronic acid heterogeneity is undesirable for mass spectrometry based quantification but can be applied for a less specific UV or fluorescence based assay. Accordingly, for a mass spectrometry-based reference assay, a second enzymatic (e.g., endoproteolytic) digest step is introduced to digest the peptide drug and produce a homogeneous peptide digest product (e.g., the 19-amino acid C-terminal peptide digest product DFIEWLKAGGPSSGAPPPS-NH2 (FIG. 3)). The peptide product can then be detected and quantified using assays such as, e.g., liquid chromatography/high resolution mass spectrometry (LC/MS).

In one aspect, a method for determining the amount of drug present in a crosslinked hyaluronic acid-linker-peptide (xHA-L-P) prodrug formulation is provided. The method includes the steps of contacting a sample of the xHA-L-P prodrug formulation with a hyaluronoglucosidase, e.g., a hyaluronidase (HAase) or a hyaluronate (HA) lyase, to generate oligomeric hyaluronic acid-linker-peptide drug (oHA-L-P), contacting the oHA-L-P with an enzyme to generate peptide digest products of the drug, and detecting the peptide digest products to determine the amount of the drug present in the xHA-L-P prodrug formulation.

In certain exemplary embodiments, the peptide digest products are between about 2 amino acids and about 100 amino acids in length, between about 3 amino acids and about 75 amino acids in length, are between about 4 amino acids and about 50 amino acids in length, are between about 6 amino acids and about 30 amino acids in length, are between about 15 amino acids and about 20 amino acids in length, or are about 19 amino acids in length. In certain exemplary embodiments, the peptide digest products are about 1, about 2 or about 3 amino acids in length.

In certain exemplary embodiments, the step of detecting the peptide digest products is performed by a method selected from the group consisting of one or a combination of liquid chromatography-mass spectrometry (LC-MS), liquid chromatography tandem mass spectrometry (LC-MS-MS), liquid chromatography-high resolution mass spectrometry (LC-HRMS), ultraviolet (UV) absorbance and fluorescence detection.

In certain exemplary embodiments, the hyaluronoglucosidase is an HAase selected from the group consisting of HAase 1, HAase 2, HAase 3, HAase 4, HAase 5 and HAase 6. In other exemplary embodiments, the hyaluronoglucosidase is HAase 1 or HAase 2. In still other exemplary embodiments, the hyaluronoglucosidase is HAase 2. In certain exemplary embodiments, the hyaluronoglucosidase is HA lyase EC 4.2.2.1.

In certain exemplary embodiments, the oHA-L-P is contacted with an endoproteinase, e.g., Glu-C, Asp-N, Lys-C, Arg-C, trypsin or chymotrypsin. In certain exemplary embodiments, the endoproteinase is Asp-N.

In certain exemplary embodiments, the method further comprises the use of an internal standard. In certain exemplary embodiments, the internal standard comprises one or more heavy isotopes.

In certain exemplary embodiments, the amount of drug present is determined using a calibration curve.

In certain exemplary embodiments, the xHA-L-P is contacted with the hyaluronoglucosidase in a pressure cycler. In certain exemplary embodiments, pressure in the pressure cycler is greater than atmospheric pressure. In certain exemplary embodiments, the pressure is about 5 KPSI, about 10 KPSI or about 15 KPSI.

In certain exemplary embodiments, the oHA-L-P is contacted with the second enzyme in a pressure cycler. In certain exemplary embodiments, pressure in the pressure cycler is greater than atmospheric pressure. In certain exemplary embodiments, the pressure is about 35 KPSI, about 40 KPSI or about 45 KPSI.

In another aspect, a method for determining the amount of drug present in a crosslinked hyaluronic acid-linker-peptide (xHA-L-P) prodrug formulation is provided. The method includes the steps of contacting a sample of the xHA-L-P prodrug formulation with a hyaluronoglucosidase to generate oligomeric hyaluronic acid-linker-peptide drug (oHA-L-P), contacting the oHA-L-P with an endoproteinase to generate peptide digest products of the drug, and detecting the peptide digest products to determine the amount of the drug present in the xHA-L-P prodrug formulation.

In certain exemplary embodiments, the step of detecting the peptide digest products is performed by a method selected from the group consisting of one or a combination of LC-MS, LC-MS-MS, LC-HRMS, UV absorbance and fluorescence detection.

In certain exemplary embodiments, the hyaluronoglucosidase is HAase 1 or HAase 2. In certain exemplary embodiments, the hyaluronoglucosidase is HA lyase EC 4.2.2.1.

In certain exemplary embodiments, the endoproteinase is selected from the group consisting of Glu-C, Asp-N, Lys-C, Arg-C, trypsin and chymotrypsin.

In certain exemplary embodiments, the endoproteinase is Asp-N.

In certain exemplary embodiments, the method further comprises the use of an internal standard. In certain exemplary embodiments, wherein the internal standard comprises one or more heavy isotopes.

In certain exemplary embodiments, the amount of drug present is determined using a calibration curve.

In certain exemplary embodiments, the xHA-L-P is contacted with the hyaluronoglucosidase in a pressure cycler. In certain exemplary embodiments, pressure in the pressure cycler is greater than atmospheric pressure. In certain exemplary embodiments, the pressure is about 5 KPSI, about 10 KPSI or about 15 KPSI.

In certain exemplary embodiments, the oHA-L-P is contacted with the endoproteinase in a pressure cycler. In certain exemplary embodiments, pressure in the pressure cycler is greater than atmospheric pressure. In certain exemplary embodiments, the pressure is about 35 KPSI, about 40 KPSI or about 45 KPSI.

In another aspect, a method for determining the amount of drug present in a crosslinked hyaluronic acid-linker-peptide (xHA-L-P) prodrug formulation is provided. The method includes the steps of contacting the xHA-L-P prodrug with hyaluronidase 2 to generate an oligomeric hyaluronic acid-linker-peptide drug (oHA-L-P), contacting the oHA-L-P with Asp-N to generate peptide digest products of the drug, and detecting the peptide digest products to determine the amount of the drug present in the xHA-L-P prodrug formulation.

In certain exemplary embodiments, the peptide digest products are between about 2 amino acids and about 100 amino acids in length, between about 3 amino acids and about 75 amino acids in length, are between about 4 amino acids and about 50 amino acids in length, between about 6 amino acids and about 30 amino acids in length, between about 15 amino acids and about 20 amino acids in length, or are about 19 amino acids in length. In certain exemplary embodiments, the peptide digest products are about 1, about 2 or about 3 amino acids in length.

In certain exemplary embodiments, the step of detecting the peptide digest products is performed by a method selected from the group consisting of one or a combination of LC-MS, LC-MS-MS, LC-HRMS, UV absorbance and fluorescence detection.

In certain exemplary embodiments, the method further comprises the use of an internal standard. In certain exemplary embodiments, the internal standard comprises one or more heavy isotopes.

In certain exemplary embodiments, the amount of drug present is determined using a calibration curve.

In certain exemplary embodiments, the xHA-L-P is contacted with the hyaluronidase 2 in a pressure cycler. In certain exemplary embodiments, pressure in the pressure cycler is greater than atmospheric pressure. In certain exemplary embodiments, the pressure is about 5 KPSI, about 10 KPSI or about 15 KPSI.

In certain exemplary embodiments, the oHA-L-P is contacted with the Asp-N in a pressure cycler. In certain exemplary embodiments, pressure in the pressure cycler is greater than atmospheric pressure. In certain exemplary embodiments, the pressure is about 35 KPSI, about 40 KPSI or about 45 KPSI.

In another aspect, a method for determining the amount of drug present in a crosslinked hyaluronic acid-linker-peptide (xHA-L-P) prodrug formulation is provided. The method includes the steps of contacting the xHA-L-P prodrug with HA lyase EC 4.2.2.1 to generate an oligomeric hyaluronic acid-linker-peptide drug (oHA-L-P), contacting the oHA-L-P with Asp-N to generate peptide digest products of the drug, and detecting the peptide digest products to determine the amount of the drug present in the xHA-L-P prodrug formulation.

In certain exemplary embodiments, the peptide digest products are between about 2 amino acids and about 100 amino acids in length, between about 3 amino acids and about 75 amino acids in length, are between about 4 amino acids and about 50 amino acids in length, between about 6 amino acids and about 30 amino acids in length, between about 15 amino acids and about 20 amino acids in length, or are about 19 amino acids in length. In certain exemplary embodiments, the peptide digest products are about 1, about 2 or about 3 amino acids in length.

In certain exemplary embodiments, the step of detecting the peptide digest products is performed by a method selected from the group consisting of one or a combination of LC-MS, LC-MS-MS, LC-HRMS, UV absorbance and fluorescence detection.

In certain exemplary embodiments, the method further comprises the use of an internal standard. In certain exemplary embodiments, the internal standard comprises one or more heavy isotopes.

In certain exemplary embodiments, the amount of drug present is determined using a calibration curve.

In certain exemplary embodiments, the xHA-L-P is contacted with the HA lyase EC 4.2.2.1 in a pressure cycler. In certain exemplary embodiments, pressure in the pressure cycler is greater than atmospheric pressure. In certain exemplary embodiments, the pressure is about 5 KPSI, about 10 KPSI or about 15 KPSI.

In certain exemplary embodiments, the oHA-L-P is contacted with the Asp-N in a pressure cycler. In certain exemplary embodiments, pressure in the pressure cycler is greater than atmospheric pressure. In certain exemplary embodiments, the pressure is about 35 KPSI, about 40 KPSI or about 45 KPSI.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 7A shows HA digested with HAase 1, with a C-terminal Asp-N digest product added. FIG. 7B shows HA digested with HAase 2, with a C-terminal Asp-N digest product added. FIG. 7C is a control showing intact SAR425899 digested with Asp-N in buffer. FIG. 7D shows HA digested with HAase 1, with intact SAR425899 peptide added. Asp-N digestion was then performed. FIG. 7E shows HA digested with HAase 2, with intact SAR425899 peptide added. Asp-N digestion was then performed. FIG. 7F is a control showing intact SAR425899 digested with Asp-N in buffer. The same C-terminal peptide intensity level was observed for the two HAase digests spiked with C-terminal peptide and the control and for the two HAase digests spiked with SAR425899 and control digested with Asp-N.

FIG. 8A shows HA-linker-SAR425899 digested with HAase 1, followed by digestion with Asp-N. FIG. 8B shows HA-linker-SAR425899 digested with HAase 2, followed by digestion with Asp-N. The C-terminal Asp-N digest product is shown by the peaks at 956.99 m/z.

FIG. 9A shows that acceptable linearity was observed for the standard C-terminal peptide curve from 10 ng/mL to 10 μg/mL. FIG. 9B shows very good fragmentation of the Asp-N digest-derived C-terminal peptide, making it suitable for multiple reaction monitoring (MRM) methods.

FIG. 11A depicts raw data. FIG. 11B depicts a graphical representation of curves in matrix and curves in buffer. Excellent linearity was observed. The curve slopes deviated from each other by 3.1%. The matrix effect was, therefore, insignificant, and the buffer curves could be applied for quantitative analysis.

Figure 1:
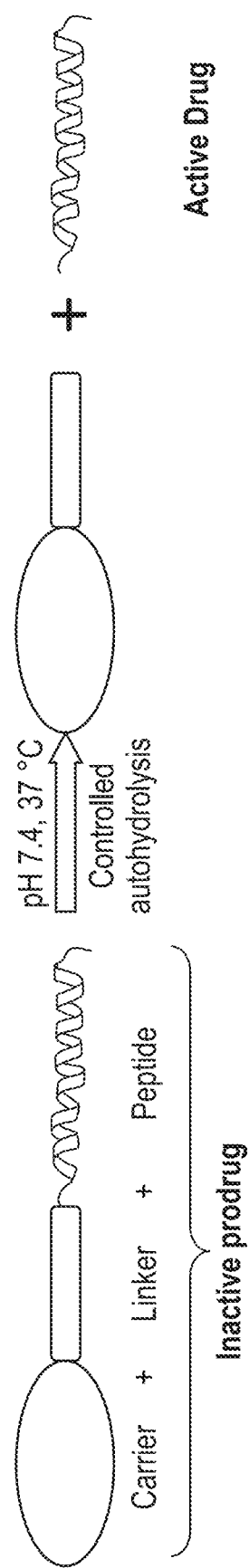
FIG. 1 depicts a polymeric carrier and a self-cleaving linker that slowly releases active peptide drug (i.e., a once daily GLP-1/GCC receptor agonist, SAR425899) from an inactive prodrug form in vivo.

DETAILED DESCRIPTION

The present invention is based on the development of a novel quantification method for determining the amount of drug loaded on a polymer. In certain embodiments, the method comprises cleaving hyaluronic acids (HAs) present in a sample of crosslinked hyaluronic acid-linker-peptide drug (xHA-L-P) to form a heterogeneous mixture of oligomeric hyaluronic acid-linker-peptide drug (oHA-L-P). The oHA-L-P may then be proteolytically digested to yield a homogenous peptide digest product that can be detected and quantified using well-known methods in the art such as, e.g., liquid chromatography, mass spectrometry, UV absorbance, fluorescence-based assays and the like. In particularly exemplary embodiments, compositions comprising xHA-L-P (e.g., the SAR425899 prodrug) are provided in which "P" is the peptide drug SAR425899, "L" is a self-cleaving crosslinker, and "xHA" is crosslinked hyaluronic acid (FIG. 2).

As used herein, the term "prodrug" is intended to refer to a compound that undergoes biotransformation before exhibiting its pharmacological effects. Prodrugs can thus be viewed as biologically active moieties containing specialized non-toxic protective groups used in a transient manner to alter or to eliminate undesirable properties in the parent molecule. Typical prodrugs may be a carrier-linked prodrug that contains a temporary linkage of a given active substance with a transient carrier group that produces improved physicochemical or pharmacokinetic properties and that can be easily removed in vivo, usually by a hydrolytic cleavage; a cascade prodrug for which the cleavage of the carrier group becomes effective only after unmasking an activating group.

To enhance physicochemical or pharmacokinetic properties of a drug such as SAR425899 in vivo, such drug can be conjugated with a carrier (e.g., xHA). If the drug is transiently bound to a carrier and/or a linker, such systems are commonly assigned as carrier-linked prodrugs. According to the definitions provided by IUPAC, a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in carrier-linked prodrugs described herein can be any known cleavable linker or non-cleavable linker, e.g., enzyme labile linkers (e.g., acid-cleavable linkers, reducible linkers (e.g., disulfide linkers), β-glucuronide linkers, and the like), photo-cleavable linkers, thioether linkers, maleimidocaproyl linkers, peptide linkers (e.g., dipeptide linkers), crosslinkers and the like. Suitable linkers are commercially available from a variety of vendors such as, e.g., Sigma-Aldrich, Millipore Sigma, Creative Biolabs and the like.

In certain exemplary embodiments, the linkers employed in carrier-linked prodrugs described herein are transient (e.g., self-cleavable), meaning that they are non-enzymatically, hydrolytically degradable (cleavable) under physiological conditions with half-lives ranging from, for example, one hour to three months.

As used herein, "physiological conditions" refer to the temperature, pH and the like with respect to a particular environment of the body where a drug is intended to be released. For example, release in the plasma would occur at a pH of between 7.35 and 7.45 at a temperature of about 37° C. (e.g., between about 36° C. and about 38° C.), and release in a lysosome would occur at a pH of between about 6.5 to about 4.5 at a temperature of about 37° C.

In certain exemplary embodiments, a drug (e.g., a peptide drug) is transiently linked to a hydrogel carrier via a self-cleaving linker, e.g., an xHA hydrogel carrier. The terms "hydrogel prodrug" and "hydrogel-linked prodrug" refer to prodrugs of biologically active agents transiently linked to a hydrogel and are used synonymously.

The terms "drug," "peptide drug," "biologically active molecule," "biologically active moiety," "biologically active agent," "active agent" and the like, refer to any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. In certain exemplary embodiments, the terms "drug," "biologically active molecule," "biologically active moiety," "biologically active agent," "active agent," and the like refer to a peptide drug such as, e.g., SAR425899.

A "free form" of a drug refers to a drug (e.g., SAR425899) in its unmodified, pharmacologically active form, such as after being released from a hydrogel conjugate prodrug (e.g., SAR425899 prodrug).

As used herein, the phrase "anti-cancer therapeutic agent" or "anti-cancer agent" refers to a molecule which is detrimental to the growth and/or proliferation of neoplastic or tumor or cancer cells and may act to reduce, inhibit or destroy malignancy.

As used herein, the term "cytostatic" refers to a molecule that inhibits cell growth and multiplication.

As used herein, the phrase "cytotoxic nucleoside" refers to a nucleobase or nucleoside analogue that exerts cytotoxic effects by mimicking endogenous nucleosides.

As used herein, the phrase "tubulin binding agent" refers to a molecule that associates directly with the tubulin system.

As used herein, the term "hormone" refers to any member of a class of signaling molecules that are produced by glands in multicellular organisms and that are transported by the circulatory system to target distant organs to regulate physiology and/or behavior. A "hormone antagonist" is a specific type of receptor antagonist which acts upon hormone receptors.

As used herein, the phrase "anti-angiogenesis agent" refers to a molecule that inhibits the physiological process of angiogenesis, through which new blood vessels form from pre-existing vessels.

As used herein, the phrase "enzyme inhibitor" refers to a molecule that inhibits the function of a particular enzyme.

As used herein, the phrase "gene regulator" refers to a molecule that can positively or negatively influence the transcription of a gene.

As used herein, the phrase "cytotoxic therapeutic agent" refers to a substance that inhibits or prevents the function of cells and/or causes destruction of cells. The term "cytotoxic agent" is intended to include chemotherapeutic agents, enzymes, antibiotics, and toxins such as small molecule toxins or enzymatically active toxins of bacterial, fungal, plant or animal origin, including fragments and/or variants thereof, and the various antitumor or anti-cancer agents disclosed below. In some embodiments, the cytotoxic agent is a taxoid, a vincas, a maytansinoid or maytansinoid analog such as DM1 or DM4, a small drug, a leptomycin derivative, an auristatin or dolastatin analog, a prodrug, topoisomerase II inhibitors, a DNA alkylating agent, an anti-tubulin agent, a CC-1065 or CC-1065 analog.

As used herein, the phrase "pharmaceutically-acceptable carrier" refers to any and all solvents, dispersion media, coatings, antibacterial and antifungal agents, and the like that are physiologically compatible. Examples of suitable carriers, diluents and/or excipients include one or more of water, amino acids, saline, phosphate buffered saline, buffer phosphate, acetate, citrate, succinate; amino acids and derivates such as histidine, arginine, glycine, proline, glycylglycine; inorganic salts NaCl, calcium chloride; sugars or polyalcohols such as dextrose, glycerol, ethanol, sucrose, trehalose, mannitol; surfactants such as Polysorbate 80, polysorbate 20, poloxamer 188; and the like, as well as combination thereof. In many cases, it will be suitable to include isotonic agents, such as sugars, polyalcohols, or sodium chloride in the composition, and formulation may also contain an antioxidant such as tryptamine and a stabilizing agent such as Tween 20.

As used herein, the terms "hyaluronic acid," "HA" and "hyaluronan" are used interchangeably, and refer to a non-sulfate linear polysaccharide composed of repeating disaccharide units of d-glucuronic acid and N-acetyl-d-glucosamine linked by β-1-3 and β-1-4 glycosidic bonds (e.g., →4)-β-d-GlcpA-(1→3)-β-d-G1cpNAc-(1→). HA occurs with different molecular weights. High molecular weight HA (HMWHA) is greater than about $1\times10^6$ Da, and low molecular weight HA (LMWHA) is about 0.8 to about $8\times10^5$ Da. Oligomeric HA is typically less than about $6\times10^3$ Da.

HA is commercially available from vendors such as Sigma-Aldrich (St. Louis, MO), Novozymes (Blair, NE) and Stanford Chemicals (Lake Forest, CA). FDA-approved HA includes, but is not limited to, Hyalovet (Boehringer Ingelheim Vetmedica, approved for veterinary use), Hylira (Hawthorn), Hylase (ECR), Hylartin V (Zoetis, approved for veterinary use), Hyvisc (Anika Therapeutics, approved for veterinary use), Legend (Bayer Animal Health, approved for veterinary use), NexHA (Vetoquinol, approved for veterinary use), Orthovisc (DePuy Mitek), ProVisc (Alcon), Shellgell (Cytosol Opthalmics), Solesta (Salix), Supartz (Bioventus), Synacid (Intervet, approved for veterinary use), Healon5 (Abbott Medical Optics), Healon GV (Abbott), Healon Endocoat (Abbott Medical Optics), Healon (Abbott), Euflexxa (Ferring Pharmaceuticals), Equron (Zoetis, approved for veterinary use), Coease (Abbott Medical Optics), Bionect (Cipher), Amvisc (Chiron), Synvisc (Genzyme), Gel-One (Zimmer Biomet), and Hyaglan (Fidia Pharma).

To improve the mechanical properties and prolong the duration of HA in vivo, a hydrogel can be formed by covalently crosslinking HA polymer chains into a three-dimensional network (see e.g. Ågerup, Berg, & Åkermark (2005) BioDrugs 19:23; Edsman et al. (2011) Cartilage 2:384). Mechanical and physical properties of crosslinked HA (xHA) hydrogels are dependent on the degrees of modification and crosslinking (La Gatta, Schiraldi, Papa, & De Rosa (2011) Polymer Degradation and Stability 96:603).

As used herein, the terms "crosslinking agent" and "crosslinker" are intended to cover a chemical agent that could react with hyaluronic acid through at least one of covalent and/or non-covalent bonds. Non-limiting examples of non-covalent bonds include ionic bonds, hydrophobic interactions, hydrogen bonds and van der Waals forces (dispersion attractions, dipole-dipole and dipole-induced interactions).

The term "crosslinked" as used herein is intended to refer to two or more polymer chains of hyaluronic acid which have been covalently and/or non-covalently bonded via a crosslinking agent. Such crosslinking is differentiated from intermolecular or intramolecular dehydration which results in lactone, anhydride, or ester formation within a single polymer chain or between two or more chains. Although, it is contemplated that intramolecular crosslinking may also occur in the compositions as described herein. Crosslinking agents contain at least two functional groups that create covalent and/or non-covalent bonds between two or more molecules (i.e. hyaluronic acid chains). In an aspect of the present disclosure, the crosslinking agents comprise complimentary functional groups to that of hyaluronic acid such that the crosslinking can proceed.

Physical crosslinking of HA can be accomplished using a variety of pH, temperature, ionic strength conditions, and physicochemical interactions, for example, hydrophobic interactions, hydrogen bonding, charge interaction, or stereocomplexation. In particular, temperature-responsive hydrogels have been extensively examined for various applications. Common thermo-gelling polymers that are frequently used to modify HA to prepare thermally sensitive HA hydrogels include poly(N-isopropylacrylamide) (PNIPAM), pluronic acid, methylcellulose, and polyethylene glycol (PEG).

Methods of crosslinking HA to form hydrogels include, but are not limited to, methods that modify —COOH groups, methods that modify —OH groups, methods that modify —NHCOCH$_3$ groups, and chemical crosslinking methods using Schiff-base crosslinking, dialdehyde hyaluronic acid (CHO-HA), thiol modifications, Diels-Alder reactions, and enzyme-mediated linking.

Methods of crosslinking HA hydrogels are described in Kenne et al. (2013) *Carb. Polymers* 91:410; and Khunmanee, Supra; Hoare T R, Kohane D S. Hydrogels in drug delivery: progress and challenges. Polymer 2008; 49(8): 1993-2007; Gupta D, Tator C H, Shoichet M S. Fast-gelling injectable blend of hyaluronan and methylcellulose for intrathecal, localized delivery to the injured spinal cord. Biomaterials 2006; 27(11): 2370-2379; Fang, J-Y, Chen, J-P, Leu, Y-L. Temperature-sensitive hydrogels composed of chitosan and hyaluronic acid as injectable carriers for drug delivery. Eur J Pharm Biopharm 2008; 68(3): 626-636; and Ha D I, Lee S B, Chong M S, et al. Preparation of thermo-responsive and injectable hydrogels based on hyaluronic acid and poly(N-isopropylacrylamide) and their drug release behaviors. Macromol. Res. 2006; 14(1): 87-93, each of which is incorporated herein by reference in its entirety for all purposes.

Crosslinked HA is commercially available from vendors such as Sigma-Aldrich (St. Louis, MO) and Stanford Chemicals (Lake Forest, CA).

As used herein the term "hydrogel" is intended to refer to a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

In certain embodiments, the methods described herein utilize one or more enzymes and/or compounds to cleave xHA, e.g., to cleave xHA present in xHA-L-P to form oHA-L-P.

Enzymes that are suitable for cleaving xHA include, but are not limited to, bacterial β-endoglycosidases, bacterial β-exoglycosidases (e.g., β-glucuronidase, β-N-acetylhexosaminidase and the like), eukaryotic β-endoglycosidases (e.g., endo-β-n-acetylhexosaminidases, β-endoglucuronidases and the like), eukaryotic β-exoglycosidases (e.g., β-exoglucuronidase, exo-β-N-acetylglucosaminidase, and the like), hyaluronidases, hyaluronoglucosidases and the like.

Non-enzymatic methods to cleave xHA include, but are not limited to, acidic hydrolysis, alkaline hydrolysis, ultrasonic degradation, thermal degradation, degradation by oxidants (e.g., superoxide anion radical, hydrogen peroxide, singlet oxygen, hydroxyl radical, nitric oxide, peroxynitrite anion, hypochlorous anion, carbonate radical anion, dichloride radical anion and the like), microwave irradiation, UV irradiation, γ-irradiation, Hg lamp irradiation and the like. (See Stern et al. (2007) *Biotechnol. Adv.* 25:537, incorporated herein by reference in its entirety for all purposes.)

In other embodiments, the methods described herein utilize one or more hyaluronoglucosidases, e.g., hyaluronidases (HAases) to cleave xHA, e.g., to cleave xHA present in xHA-L-P to form oHA-L-P. In certain exemplary embodiments, a combination of two, three, four, five or more HAases are used to cleave xHA. In other embodiments, a single HAase is used to cleave xHA.

As used herein, "hyaluronidase" refers to a hyaluronoglucosidase that cleaves the (1–>4)-linkages (EC 3.2.1.35) or (1–>3)-linkages (EC 3.2.1.36) between N-acetylglucosamine and glucuronate in order to catalyze the degradation of HA.

There are three general classes of hyaluronidases: 1. Mammalian-type hyaluronidases, (EC 3.2.1.35) which are endo-beta-N-acetylhexosaminidases with tetrasaccharides and hexasaccharides as the major end products. They have both hydrolytic and trans glycosidase activities, and can degrade hyaluronan and chondroitin sulfates (CS), specifically C4-S and C6-S; 2. Bacterial hyaluronidases (EC 4.2.99.1) degrade hyaluronan and, and to various extents, CS and DS. They are endo-beta-N-acetylhexosaminidases that operate by a beta elimination reaction that yields primarily disaccharide end products; and 3. Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: neutral active and acid active enzymes. There are six hyaluronidase-like genes in the human genome, HYAL1, HYAL2, HYAL3 HYAL4, HYALP1 and PH20/SPAM1. HYALP1 is a pseudogene, and HYAL3 has not been shown to possess enzyme activity toward any known substrates. HYAL4 is a chondroitinase and lacks activity towards hyaluronan. HYAL1 (also known as LUCA1, MPS9 and NAT6) is the prototypical acid-active enzyme and PH20 is the prototypical neutral-active enzyme. Acid active hyaluronidases, such as HYAL1 and HYAL2 lack catalytic activity at neutral pH. For example, HYAL1 has no catalytic activity in vitro over pH 4.5 (Frost et al. (1997) Anal. Biochemistry). HYAL2 is an acid active enzyme with a very low specific activity in vitro.

HYAL5 is an HAase originally discovered in mice that is located on the plasma and acrosomal membranes of acrosome-intact sperm that is released during the acrosome reaction. HYAL6 is an HAase that was also discovered in mice.

Chemical grade HAases are commercially available from vendors such as Sigma-Aldrich (St. Louis, MO), Millipore Sigma (Burlington, MA), and Calzyme Laboratories (San Luis Obispo, CA). FDA-approved HAases include, but are not limited to, Amphadase (bovine hyaluronidase; new drug application (NDA) No. 021665; Amphastar Pharmaceuticals), Hydase (bovine hyaluronidase; NDA No. 021716; Akorn Inc.), Hylenex (recombinant human hyaluronidase; NDA No. 021859; Halozyme); Vitrase (ovine hyaluronidase; NDA No. 021640; Bausch and Lomb), and Wydase (bovine hyaluronidase; NDA No. 006343; Baxter Healthcare).

Additional suitable HAases for use herein are described in: worldwide web site: brenda-enzymes.org/enzyme.php?ecno=3.2.1.35; Karl Meyer and Maurice M. Rapport's chapter on "Hyaluronidases" Advances in Enzymology—and Related Areas of Molecular Biology pp 199-236 vol. 13 (doi.org/10.1002/9780470122587.ch6); Stern and Jedrzejas Chem. Rev. 2006, 106, 818-839 Hyaluronidases: Their Genomics, Structures, and Mechanisms of Action; Stern and Jedrzejas, Chem. Rev. 2008, 108, 5061-5085; Yoshida et al (2013) "KIAA1199, A deafness gene of unknown function, is a new hyaluronan binding protein involved in hyaluronan depolymerization. Proc. Natl. Acad. Sci. U.S.A. 110, 5612-5617; Nagaoka et al. 2015 Regulation of Hyaluronan (HA) Metabolism Mediated by HYBID, doi: 10.1074/jbc.M115.673566 originally published online Oct. 30, 2015; Yoshino et al. 2018 Biochemical and Biophysical Research Communications Volume 505, Issue 1, 20 Oct. 2018; Yamaguchi et al 2019 (Matrix Biol. (2019) 78-79, 139-146 TMEM2: A missing link in hyaluronan catabolism identified?; each of which is herein incorporated by reference in its entirety for all purposes.

"Hyaluronidase lyase," "hyaluronate lyase," "HA lyase," "EC 4.2.2.1" or "HA lyase 4.2.2.1" refers to a hyaluronoglucosidase (i.e., a bacterial carbon-oxygen lyase) that cleaves hyaluronan chains at a beta-D-GalNAc-(1->4)-beta-D-GlcA bond, ultimately digesting the polysaccharide to 3-(4-deoxy-beta-D-gluc-4-enuronosyl)-N-acetyl-D-glucosamine. Hyaluronate lyases can be isolated from bacteria and *Streptomyces*, and differ from hyaluronidases from other sources by their mode of action, as they catalyze an elimination reaction, rather than hydrolysis, of the beta 1,4-glycosidic linkage between N-acetyl-beta-D-glucosamine and D-glucuronic acid residues.

In other embodiments, the methods described herein utilize one or more proteolytic enzymes, e.g., enzymes that catalyze proteolysis by cleaving peptide bonds via hydrolysis, to cleave peptide, e.g., to cleave P present in xHA-L-P to form oHA-L-P. Suitable proteases include, but are not limited to, serine proteases, cysteine proteases, threonine proteases, aspartic proteases, glutamic proteases, metalloproteases, asparagine peptide lyases and the like. Suitable proteases classified by optimal pH in which they are active include, but are not limited to, acid proteases, neutral proteases, and basic proteases. In certain exemplary embodiments, a combination of two, three, four, five or more proteolytic enzymes are used to cleave peptide. In other embodiments, a single proteolytic enzyme is used to cleave peptide.

In certain embodiments, the methods described herein utilize one or more enzymes and/or compounds to cleave a peptide drug present as a free drug or a prodrug, e.g., as free SAR425899 or as SAR425899 prodrug, in order to generate a peptide digest product of the drug or prodrug.

In certain embodiments, the methods described herein utilize one or more endoproteinases to cleave a peptide drug present as a free drug or a prodrug, e.g., as free SAR425899 or as SAR425899 prodrug, in order to generate a peptide digest product of the drug or prodrug. Criteria used to choose an appropriate endoproteinase was as follows: 1) to generate as few highly-specific fragments as possible; 2) to generate a C-terminal fragment that does not contain glutamate-palmitate linked to lysine; and 3) to use common, commercially available enzymes.

Suitable endoproteinases include, but are not limited to, Glu-C, Asp-N, Lys-C, Arg-C, trypsin and chymotrypsin. In certain exemplary embodiments, endoproteinase Asp-N is used in the methods described herein. A variety of suitable endoproteinases are commercially available from companies such as Sigma-Aldrich (St. Louis, MO), New England Biolabs (Ipswich, MA), Thermo Scientific (Lenexa, KS), and Promega (Fitchburg, WI).

In certain embodiments, a pressure cycler may be used to improve (e.g., decrease) xHA and/or oHA digest time. In certain embodiments, xHA and/or oHA digestion may be performed in a pressure cycler under cycling pressure ranging between about 5 KPSI and about 80 KPSI, e.g., at about 5 KPSI, about 10 KPSI, about 15 KPSI, about 20 KPSI, about 25 KPSI, about 30 KPSI, about 35 KPSI, about 40 KPSI, about 45 KPSI, about 50 KPSI, about 55 KPSI, about 60 KPSI, about 65 KPSI, about 70 KPSI, about 75 KPSI or about 80 KPSI.

In certain embodiments, a pressure cycler is used with one or more hyaluronoglucosidases (e.g., HAases) to digest xHA at a pressure below about 50 KPSI, below about 40 KPSI, below about 30 KPSI, or below about 20 KPSI. In certain embodiments, a pressure cycler is used with one or more hyaluronoglucosidases (e.g., HAases) to digest xHA at a pressure of about 5 KPSI, about 10 KPSI or about 15 KPSI. In certain embodiments, a pressure cycler is used with one or more hyaluronoglucosidases (e.g., HAases) to digest xHA at a pressure of about 10 KPSI.

In certain embodiments, a pressure cycler is used with one or more enzymes (e.g., endoproteinase, proteolytic enzyme, Glu-C, Asp-N, Lys-C, Arg-C, trypsin, chymotrypsin or the like) to digest peptide at a pressure below about 80 KPSI, below about 70 KPSI, below about 60 KPSI, or below about 500 KPSI. In certain embodiments, a pressure cycler is used with one or more enzymes (e.g., endoproteinase, proteolytic enzyme, Glu-C, Asp-N, Lys-C, Arg-C, trypsin, chymotrypsin or the like) to digest peptide at a pressure of about 35 KPSI, about 40 KPSI or about 45 KPSI. In certain embodiments, a pressure cycler is used with one or more enzymes (e.g., endoproteinase, proteolytic enzyme, Glu-C, Asp-N, Lys-C, Arg-C, trypsin, chymotrypsin or the like) to digest peptide at a pressure of about 40 KPSI.

In certain embodiments, a pressure cycler reduces peptide, xHA, and/or oHA digest time by at least about one hour, about two hours, about three hours, about four hours, about five hours, about six hours, about seven hours, about eight hours, about nine hours, about ten hours, about eleven hours, about twelve hours, about thirteen hours, about fourteen hours, about fifteen hours, about sixteen hours, about seventeen hours, about eighteen hours, about nineteen hours, about twenty hours, about twenty-one hours, about twenty-two hours, about twenty-three hours, about twenty-four hours or more as compared to digestion under non-pressurized conditions.

As used herein, a "peptide digest product" refers to any part or portion of a peptide drug (e.g., a free drug or a prodrug) that is generated by an enzyme and is smaller than the intact peptide drug. In certain exemplary embodiments, a peptide digest product is less than 50 amino acids long, e.g., between about 2 and about 100 amino acids in length, between about 3 and about 75 amino acids in length, between about 2 and about 50 amino acids in length, between about 4 and about 50 amino acids in length, between about 5 and about 40 amino acids in length, between about 6 and about 30 amino acids in length, or between about 15 and about 20 amino acids in length or any values or sub-ranges within these ranges. In certain exemplary embodiments, a peptide digest product is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 61, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 amino acids in length.

In particular embodiments, a peptide digest product is about 19 amino acids in length. In other particular embodiments, a peptide digest product is about 1, about 2 or about 3 amino acids in length. In yet other particular embodiments, a peptide digest product is between about 4 and about 50 amino acids in length. In still other particular embodiments, a peptide digest product is between about 15 and about 20 amino acids in length.

In certain exemplary embodiments, a peptide digest product is detected using a peptide identification method, such as liquid chromatography-mass spectrometry (LC-MS), liquid chromatography-tandem mass spectrometry (LC-MS-MS), liquid chromatography-high resolution mass spectrometry (LC-HRMS), nano-LC-MS-MS, high performance liquid chromatography-tandem MS (HPLC-MS-MS), nanoHPLC-MS-MS, ultra-performance-tandem MS (UPLC-MS-MS), nanoUPLC-MS-MS, ultra-high-performance-tandem MS (UHPLC-MS-MS), nanoUHPLC-MS-MS, ultraviolet (UV) spectrometry, fluorescence spectrometry or the like.

In certain exemplary embodiments, the methods described herein utilize a separation process such as a chromatography method, e.g., liquid chromatography. According to an embodiment, detecting peptide digest products is performed by: (i) high performance liquid chromatography ("HPLC"), (ii) anion exchange, (iii) anion exchange chromatography; (iv) cation exchange; (v) cation exchange chromatography; (vi) ion pair reversed-phase chromatography; (vii) chromatography; (viii) single dimensional electrophoresis; (ix) multi-dimensional electrophoresis; (x) size exclusion; (xi) affinity; (xii) reverse phase chromatography; (xiii) capillary electrophoresis chromatography ("CEC"); (xiv) electrophoresis; (xv) ion mobility separation; (xvi) field asymmetric ion mobility separation or spectrometry ("FAIMS"); (xvii) capillary electrophoresis; and (xviii) supercritical fluid chromatography.

The amount of peptide digest product can be determined by measurement of multiple reaction monitoring (MRM) transitions consisting of the peptide precursor ion, one or more fragment ions and a retention time. This measurement is performed, for example, on a triple quadrupole instrument. The signature can also be obtained by a combination of retention time and accurate high-resolution mass spectrometric analysis of the intact peptide. These quantitation methods typically require a labeled internal standard and an external synthetic peptide calibration curve.

In certain exemplary embodiments, internal standards are used that include a labeled peptide corresponding to a peptide drug, e.g., a labeled C-terminal peptide corresponding to the C-terminal Asp-N digest product of SAR425899. The internal standards typically have a known peptide sequence and are provided in a known quantity. In some embodiments, the standards are labeled, such with one or more heavy isotopes, e.g., $^{13}C$ or $^{15}N$.

The peptide digest product profiling methods described herein are useful for measuring the amount of drug present in a hydrogel prodrug formulation. The methods described herein are also useful for performing batch-to-batch reproducibility assessments.

As used herein, a "sample" refers to any composition containing a peptide drug (e.g., in a prodrug form). Exemplary samples include, but are not limited to, pharmaceutical compositions, dissolution or release media and the like. In certain embodiments, a sample is a hydrogel. In other embodiments, a sample is aqueous.

A sample for use in the quantification methods described herein can be a therapeutic composition, such as a liquid formulation for administration orally, sublingually, mucosally, intradermally, subcutaneously, intravenously, intramuscularly, parenterally or by inhalation.

In other embodiments, the sample will include a substrate, such as a nanoparticle, a capsule, a film or tablet, or a gel, such as a hydrogel (e.g., an xHA hydrogel). The quantification methods described herein are useful to quantify the amount of peptide drug in the substrate, such as, e.g., in a nanoparticle or capsule, or in a film or a hydrogel (e.g., an xHA hydrogel). The release can be from the interior of the substrate, e.g., an xHA hydrogel, or from the exterior (e.g., a surface) of a substrate. In one embodiment, a release profile is assayed by performing a complete release of peptide drug and then assaying for a controlled release, such as over a period of time or in different culture or solution conditions (e.g., at different temperatures, pH or the like). The amount of peptide drug released in the controlled release assay is typically reported as a fraction or percentage as compared to the amount of peptide drug released under the complete release conditions.

As used herein, "dissolution medium," "dissolution media," "release medium" and "release media" refer to a composition that is used to provide in vitro drug release information. Dissolution or release media is useful, for example, for quality control testing of a sample for determining the release and/or stability of peptide drug in a sample. In choosing a suitable dissolution or release medium, it is useful to determine the analytical target profile of the peptide drug (e.g., delayed release, constant release, extended release and the like) and/or the peptide drug solubility profile. For a review of dissolution media selection, see Martin and Gray (Summer 2011) *Journal of Validation Technology*.

As used herein, "release rate" refers to the rate that a peptide drug flows from a hydrogel prodrug formulation and into a surrounding medium in an in vitro release test. In one exemplary embodiment, the composition is first prepared for release testing by suspending the composition into the appropriate in vitro release medium. This is generally performed by exchanging the buffer after centrifugation to pellet the substrate (e.g., a hydrogel), and reconstituting the substrate using mild conditions. In certain embodiments, the assay is started by suspending the sample at 37° C. in an appropriate temperature-controlled apparatus. A sample is typically removed at various time points.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLE I

Quantification of Peptide Drug Present in Prodrug Formulation

Figure 2:
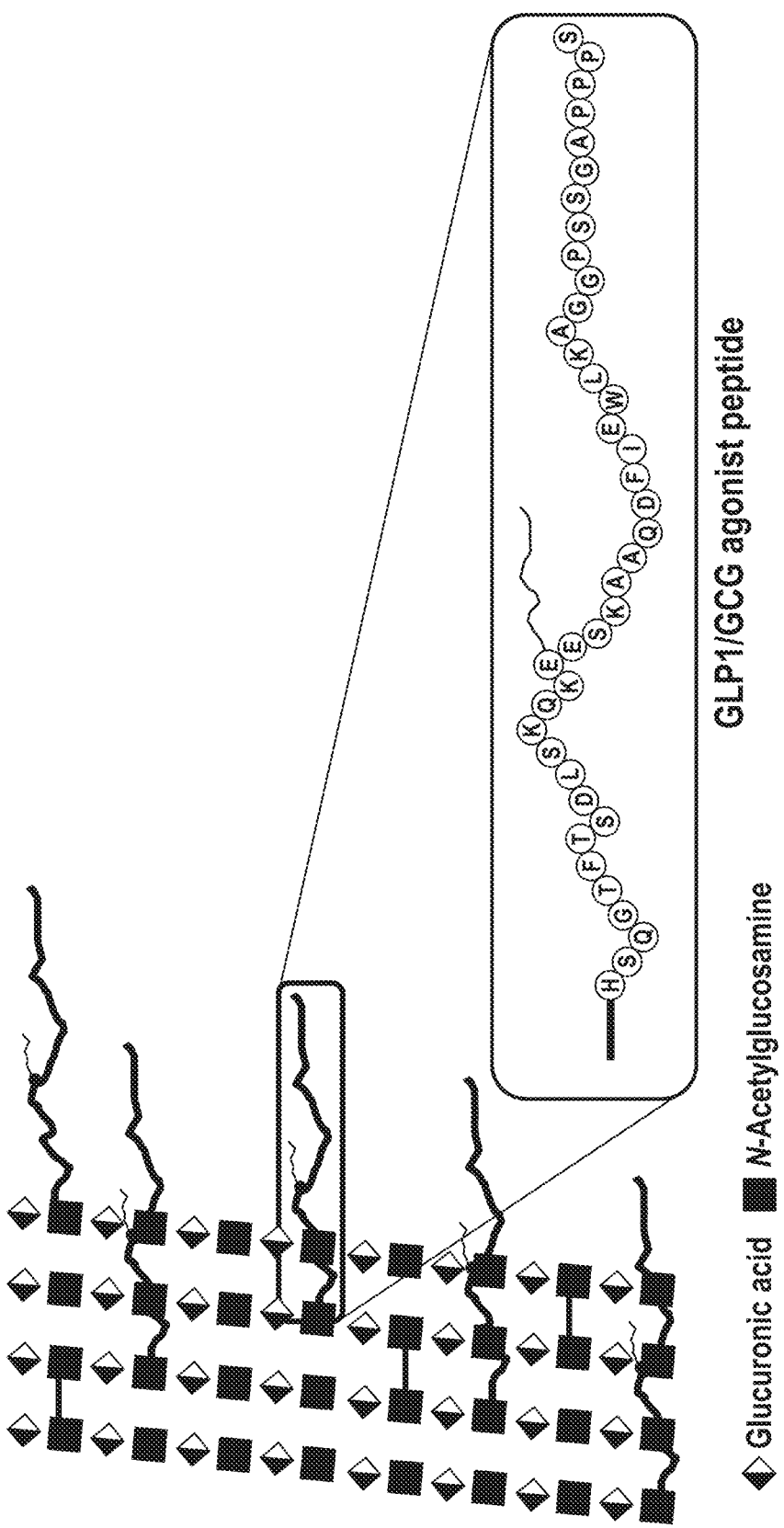
FIG. 2 depicts the complexity and size of a once-weekly GLP-1/GCG agonist (i.e., SAR425899) according to certain exemplary embodiments that is bound to a high molecular weight crosslinked hyaluronic acid hydrogel via cleavable linkers. D-serine is the amino acid in position 2 of SAR425899 (HdSQGTFTSDLSKQK(γE-palmitate)ES-KAAQ DFIEWLKAGGPSSGAPPPS-NH2).

SAR425899 is a dual receptor agonist targeting the glucagon and GLP1 receptors. Due to rapid clearance, a once daily dose is required. To reduce frequency of dosing, the once daily SAR425899 peptide drug candidate (FIG. 1) was bound to a polymeric carrier (crosslinked hyaluronic acid (xHA)) via a self-cleaving linker to provide slow release of an active peptide drug from the inactive prodrug (FIG. 2). The SAR425899 prodrug comprises crosslinked hyaluronic acid (xHA) bound to the SAR425899 lipopeptide (P) via a self-cleavable linker (L).

Determination of peptide load of a hydrogel is required for dosing and quality control. Crosslinked hyaluronic acid forms a multimillion Dalton hydrogel in an aqueous environment. Simple UV measurements typically applied for basic quantification of peptides in solution cannot be applied for hydrogels as this analysis require the hydrogel-linker-peptide to be fully dissolved. Whereas the linker is self-cleaving, complete cleavage under physiological conditions is by design very slow and therefore not suitable for analytical quantification methods which require certainty that a complete release has been accomplished.

To address this analytical challenge and enable peptide load determination, a novel method was developed that allows accurate quantification of peptide drug load in a biopolymeric prodrug measured as weight/weight percentage. The biopolymer-linker-peptide drug can, in principle, be applied to any small molecule (e.g., polypeptide, polynucleotide or the like) drug that can by cleaved or hydrolyzed, and the method can broadly be applied for drug load determination of biopolymer-containing prodrugs.

Figure 3:
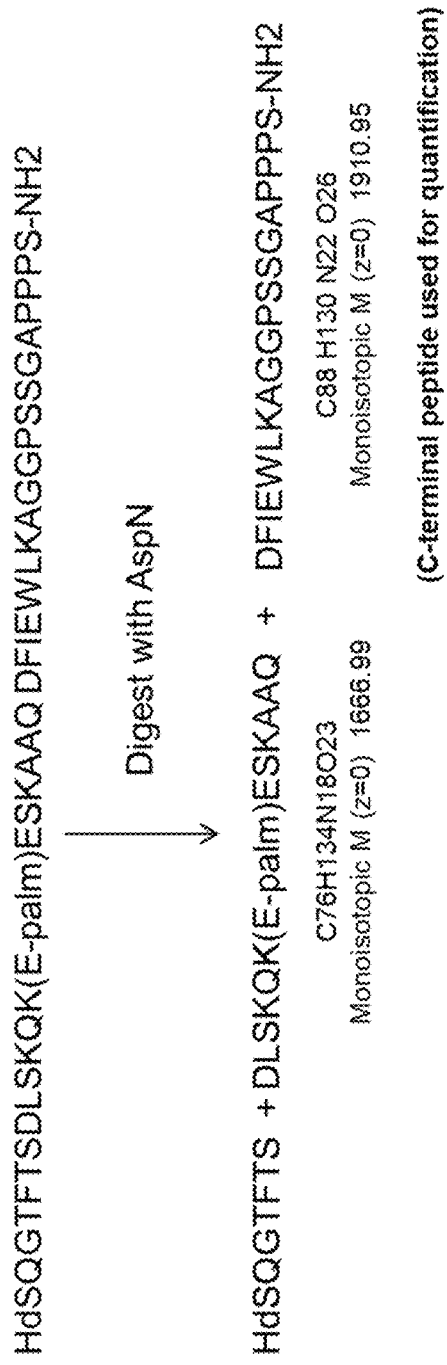
FIG. 3 schematically depicts digestion of SAR425899 with the endoproteinase Asp-N to produce digestion products, including the C-terminal peptide used for quantification. D-serine is the amino acid in position 2 of SAR425 899 (HdSQGTFTSDLSKQK(γE-palmitate)ESKAAQDFIEW-LKAGGPSSGAPPPS-NH2). Calibration curves are generated using synthetic unlabeled C-terminal peptide corresponding to the proteolytic digest product, and a heavy isotope-labeled C-terminal peptide is applied as an internal standard. 20 to 40 μg of peptide was digested with 1.20 to 0.4 μg of Asp-N (Sigma-Aldrich) (ratio 1:100) in 100 mM ammonium bicarbonate at 37° C. overnight or using a Pressure Bio Cycler at alternating between atmospheric pressure and 40 KPSI, 1 min cycling times, 37° C., for 1 hour.

The method is based on double enzymatic digestion followed by quantification of a digestion product representing the peptide. Initially, crosslinked hyaluronic acid-linker-peptide (xHA-L-P) is digested with an enzyme that digests the crosslinked hyaluronic acid. Subsequently, a proteolytic enzyme is applied to digest the attached peptide and produce proteolytic digest products. These proteolytic digest products, representing the peptide, are subsequently quantified.

xHA-L-P is weighed and partially dissolved as a hydrogel in buffer. The hydrogel is enzymatically degraded into a plurality of oligomeric hyaluronic acid-linker-peptides (oHA-L-Ps) which are soluble. The resulting hyaluronic acid oligomers of oHA-L-P is a heterogeneous mixture, consisting of peptide, linker and oligomers of hyaluronic acid of different lengths. The oligomeric hyaluronic acid heterogeneity is undesirable for quantification, and for this reason a second enzymatic (e.g., proteolytic) digest step is introduced where the peptide drug moiety is digested to produce a homogeneous 19 amino acid C-terminal peptide digest product DFIE . . . PPPS-NH$_2$ (FIG. 3). This C-terminal peptide is detected and quantified using LC/HRMS.

Figure 5:
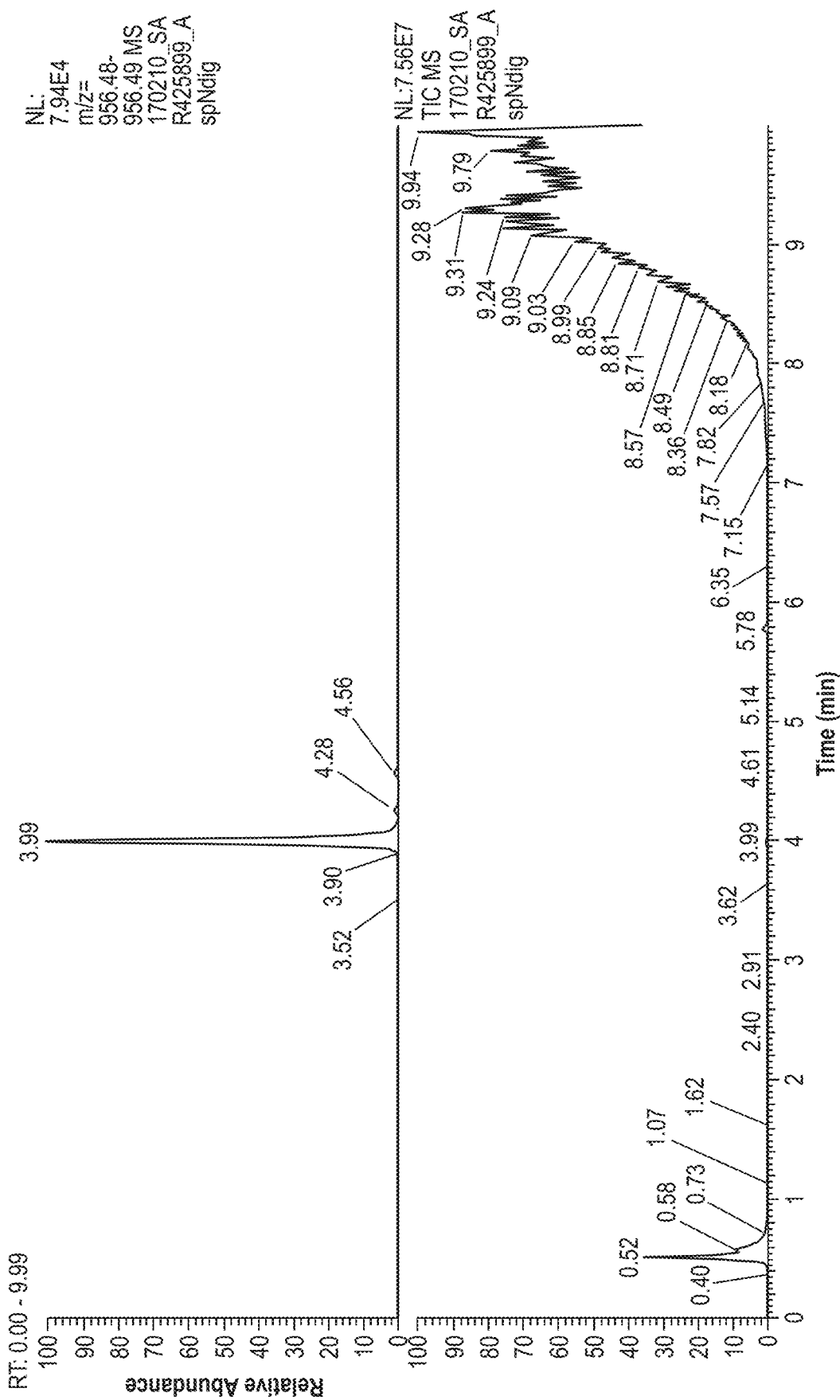
FIG. 5 shows that digestion of the SAR425899 prodrug with Asp-N produces a liquid chromatography/mass spectrometry (LC/MS)-detectable C-terminal peptide digest product. SAR425899 prodrug is xHA-linker-SAR425899; SAR425899 is HdSQGTFTSDLSKQK(E-palm)ES-KAAQDFIEWLKAGGPSSGAPPPS-NH$_2$. The C-terminal peptide digest product of HA-linker-SAR425899 digestion with Asp-N could be detected by LC/MC, showing a modest yield.

Digestion of the prodrug using Asp-N without prior hyaluronoglucosidase treatment produced a low yield of C-terminal peptide, presumably due to steric hindrance of Asp-N activity by the crosslinked hyaluronic acid (FIG. 5). Hydrolysis of linker was determined to be impractical as a peptide release method for quantification.

Figure 6:
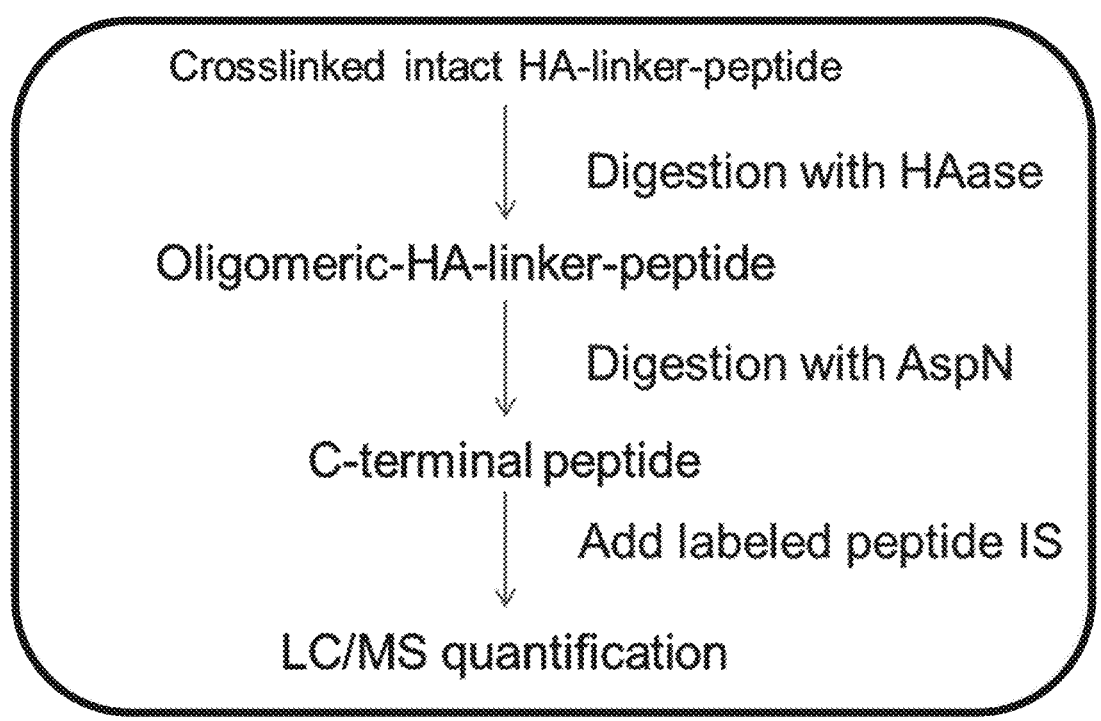
FIG. 6 schematically depicts quantification of an SAR425899 prodrug cleavage. Labeled peptide internal standard (IS) refers to a $^{13}C^{15}N$-Lys labeled C-terminal peptide. 200 nt of 1 mg/mL HA-linker peptide was digested with 30 μL 100 U/mL hyaluronate lyase EC 4.2.2.1 (Sigma-Aldrich) in 100 mM ammonium bicarbonate for 24 hours at 37° C. Asp-N digestion was subsequently performed.
Figure 7A:
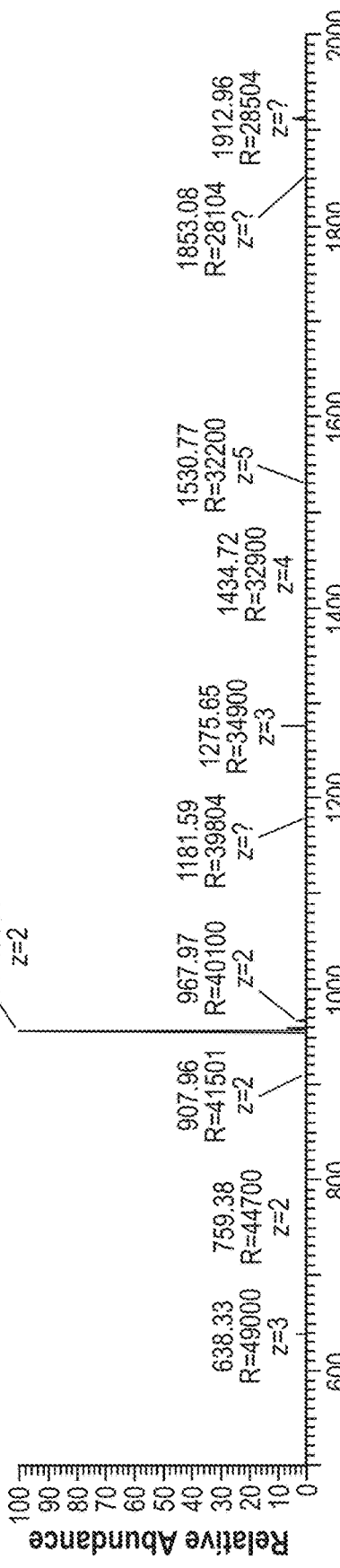
FIG. 7A-FIG. 7F show that HA digest products did not produce major matrix effects.
Figure 7A:
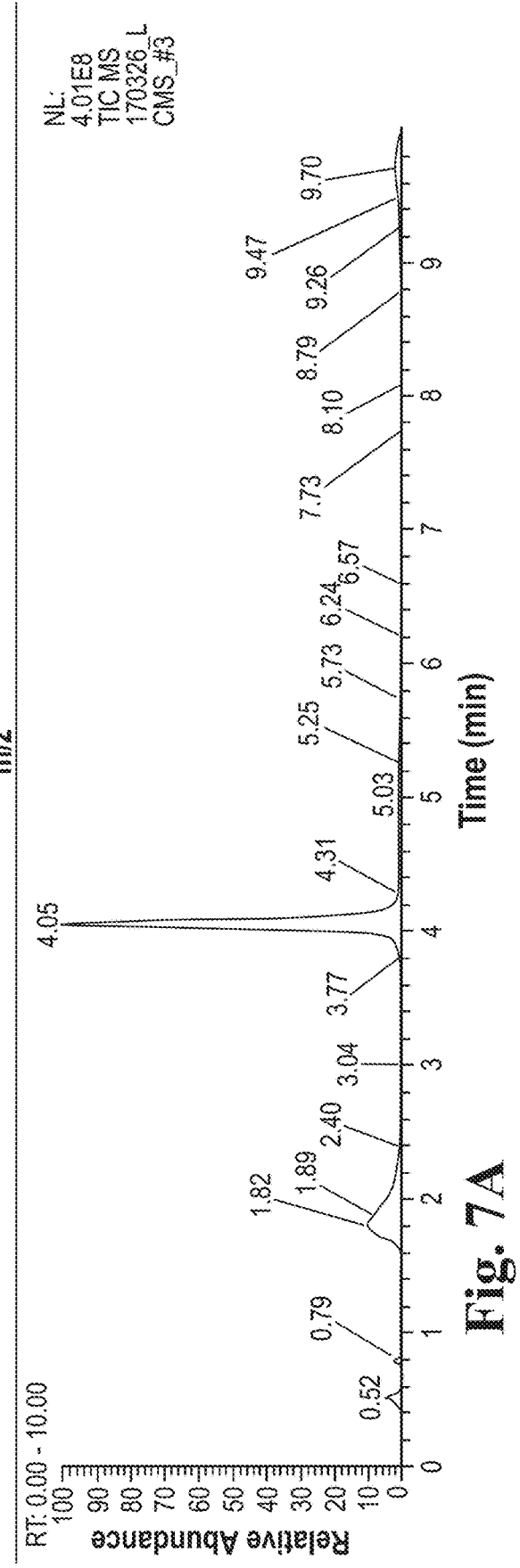
Figure 7B:
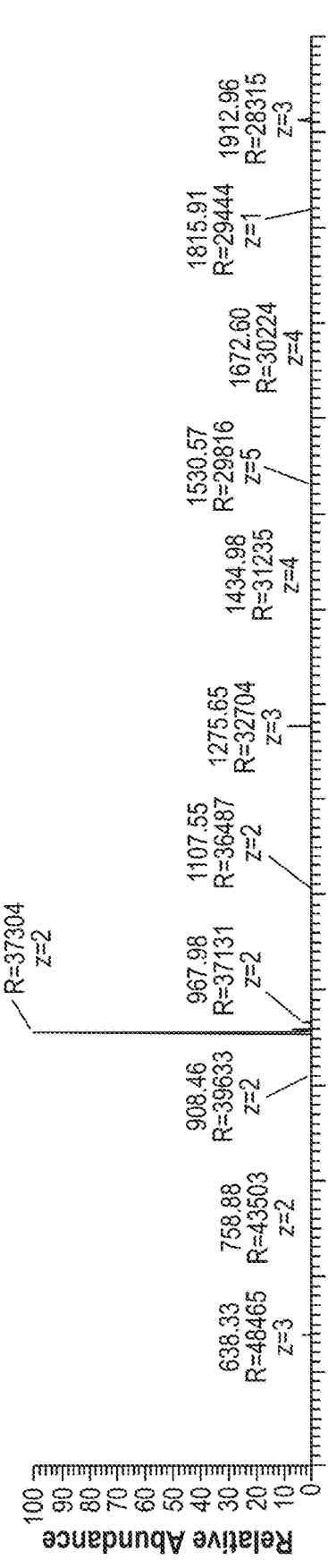
Figure 7B:
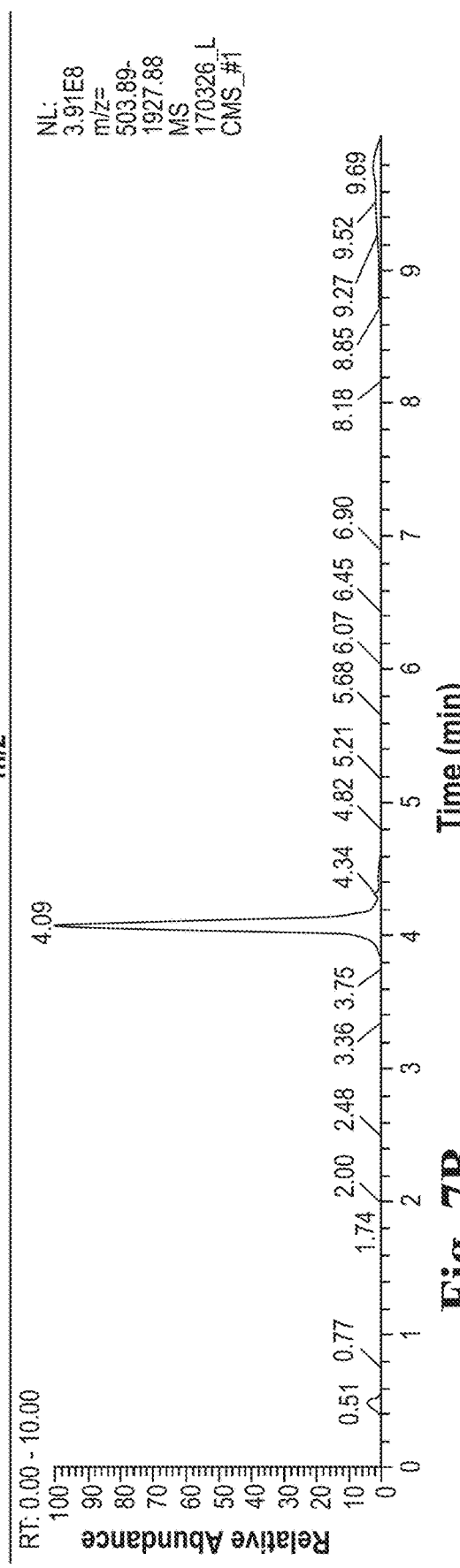
Figure 7C:
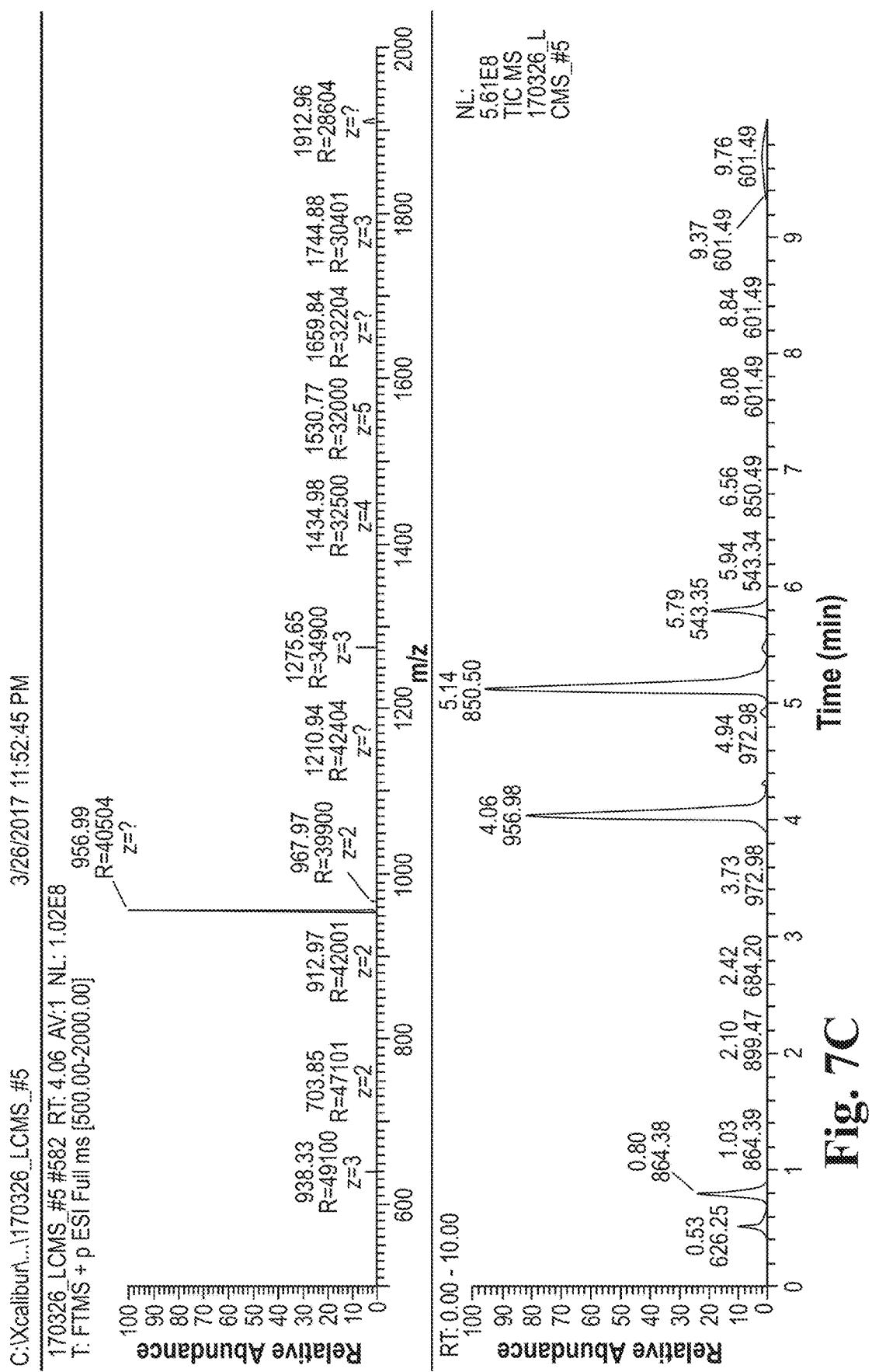
Figure 7D:
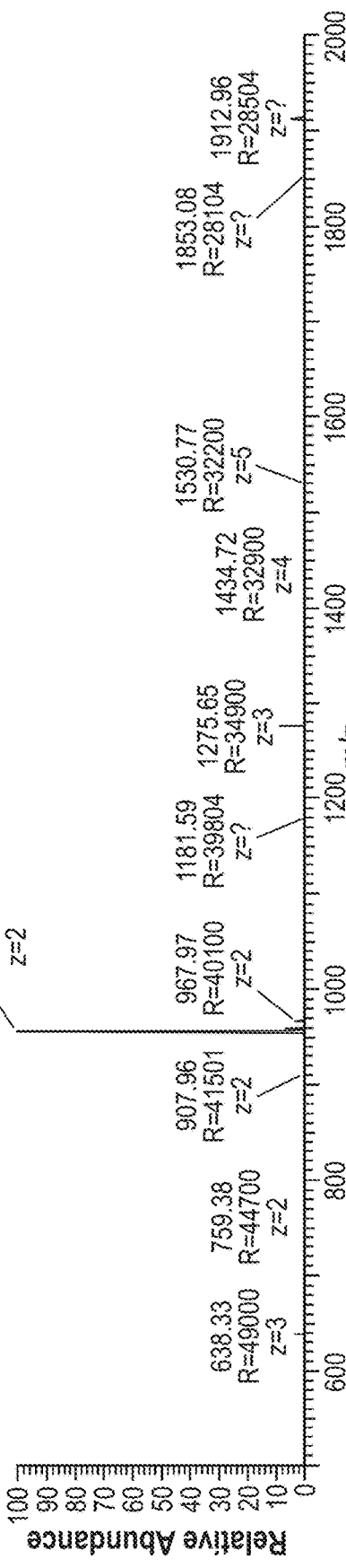
Figure 7D:
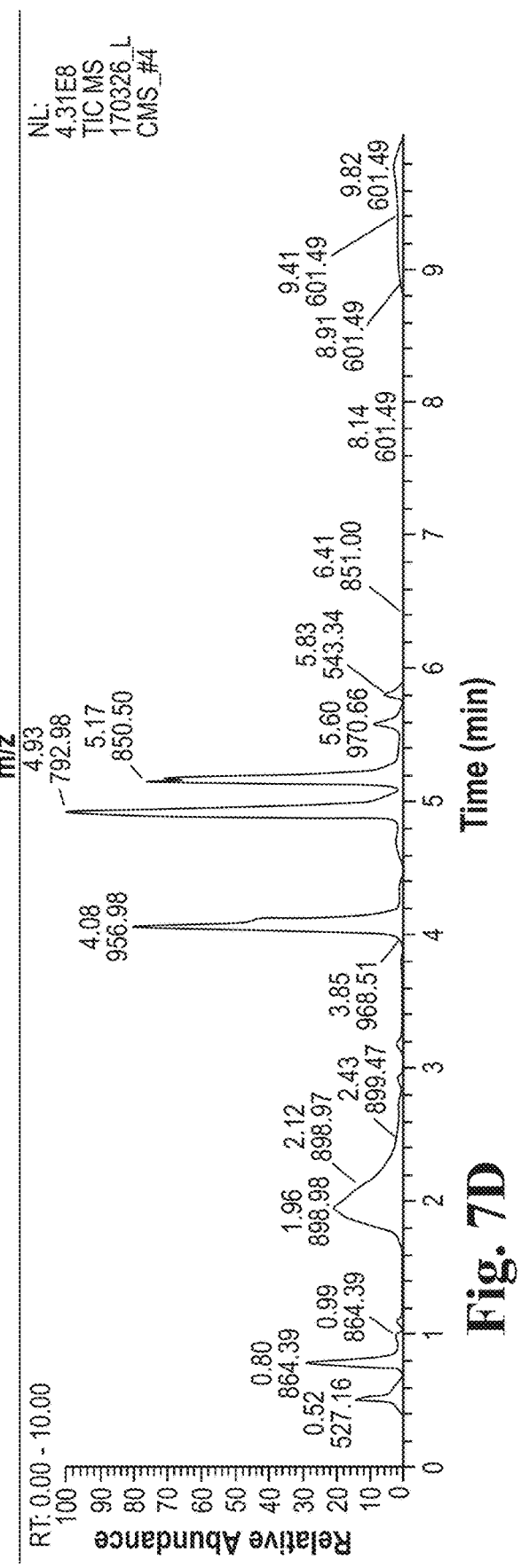
Figure 7E:
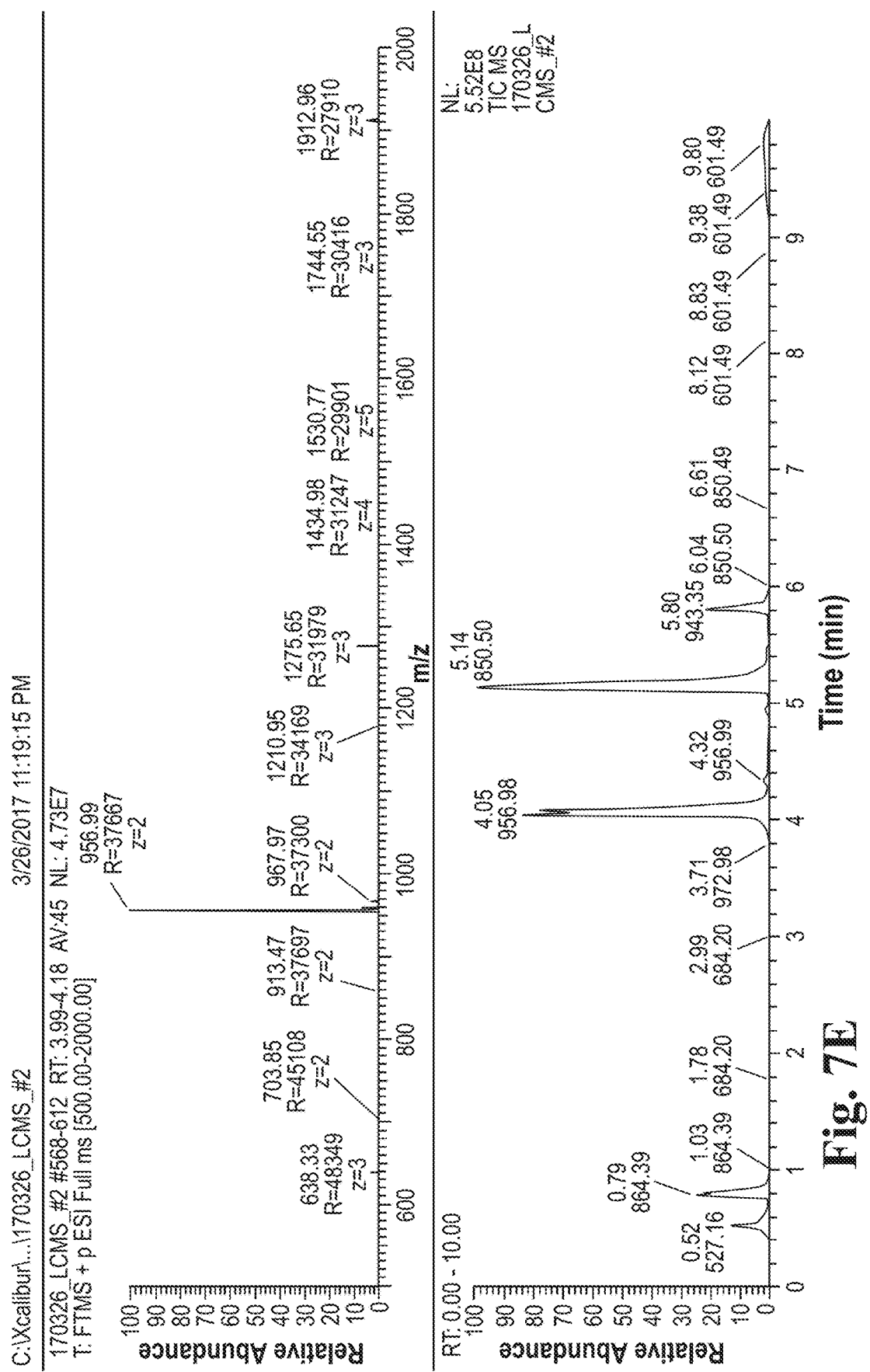
Figure 7F:
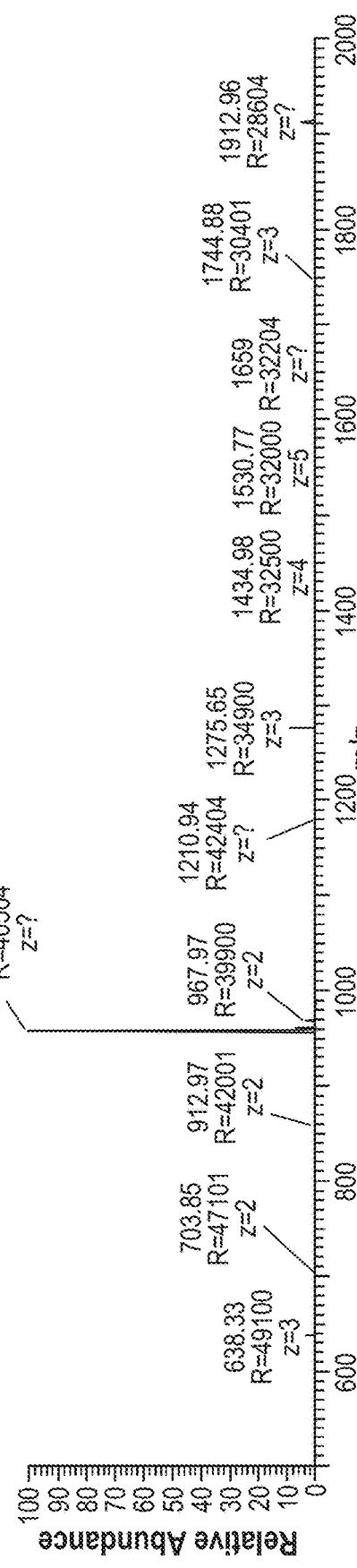
Figure 7F:
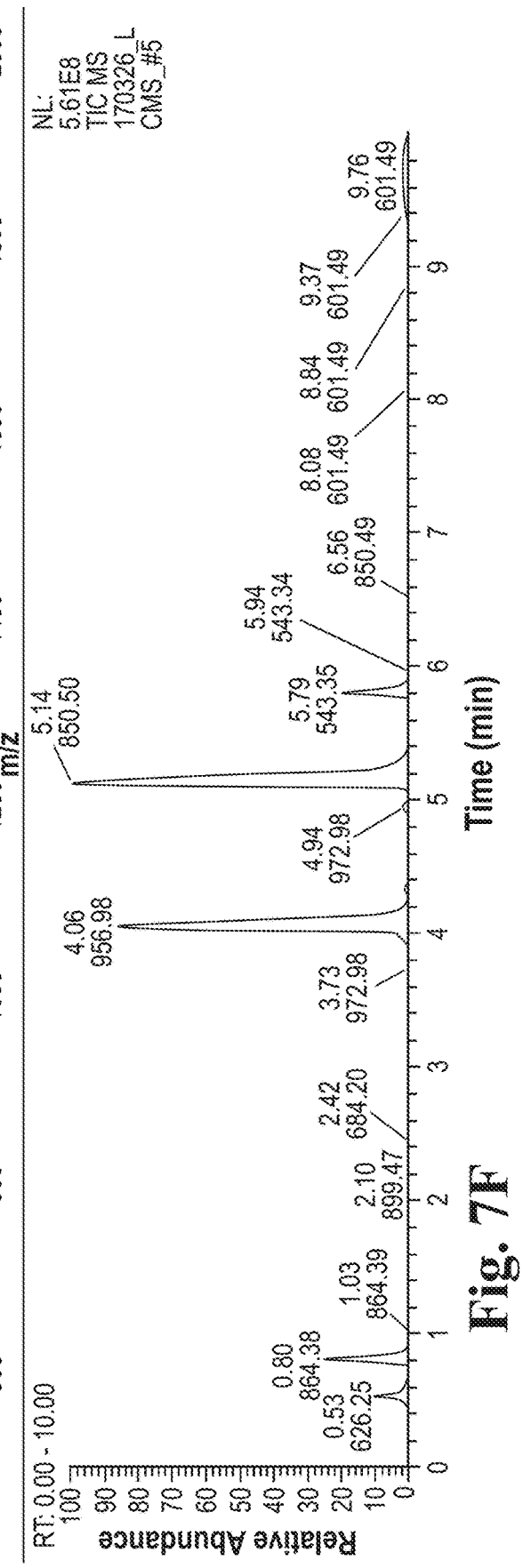

An HA digestion method was developed. (FIG. 6.) Digestion conditions that were suitable for subsequent endoproteinase (e.g., Asp-N) digestion were used. Several enzymes (e.g., HAases) capable of digesting HA were tested.

Figure 8A:
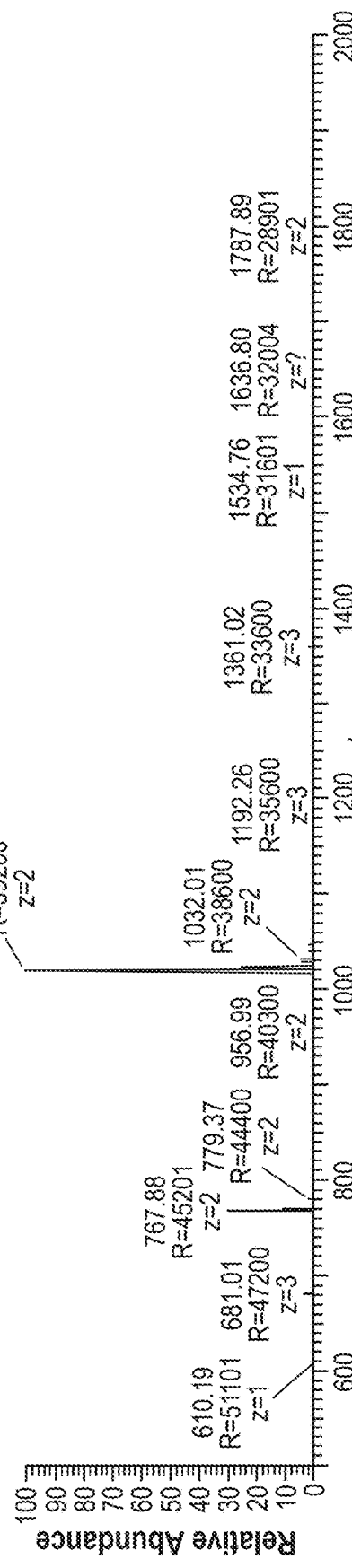
FIG. 8A-FIG. 8B show that HAase 2 produced improved subsequent Asp-N digestion as compared to HAase 1.
Figure 8A:
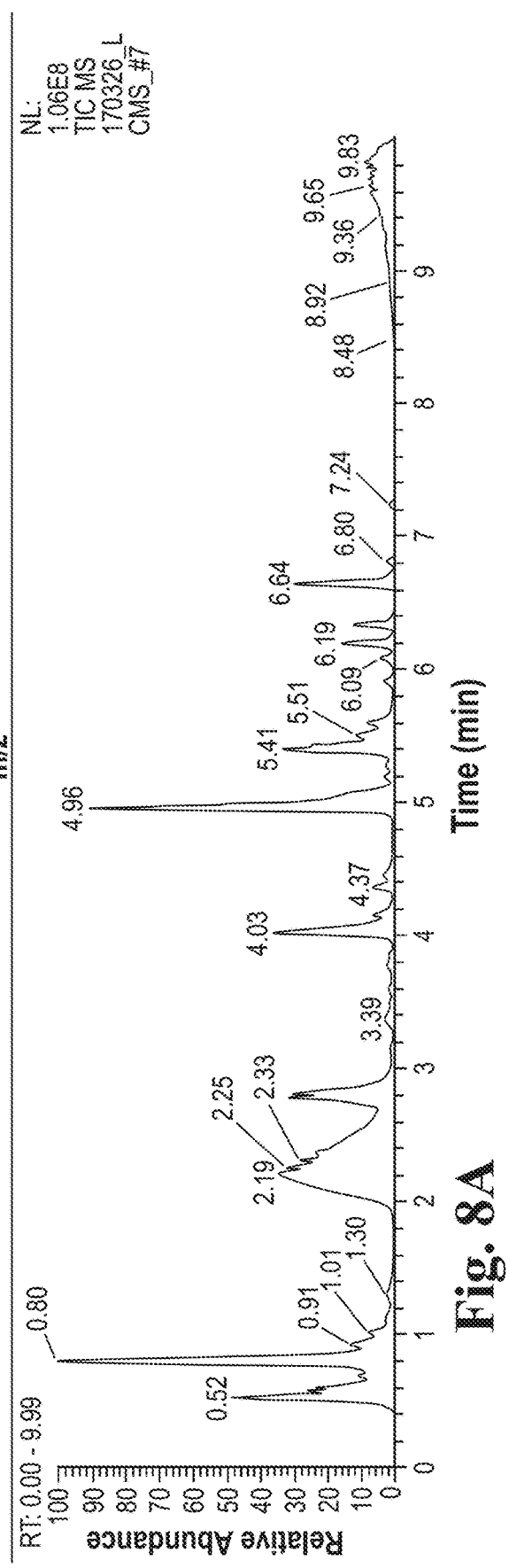
Figure 8B:
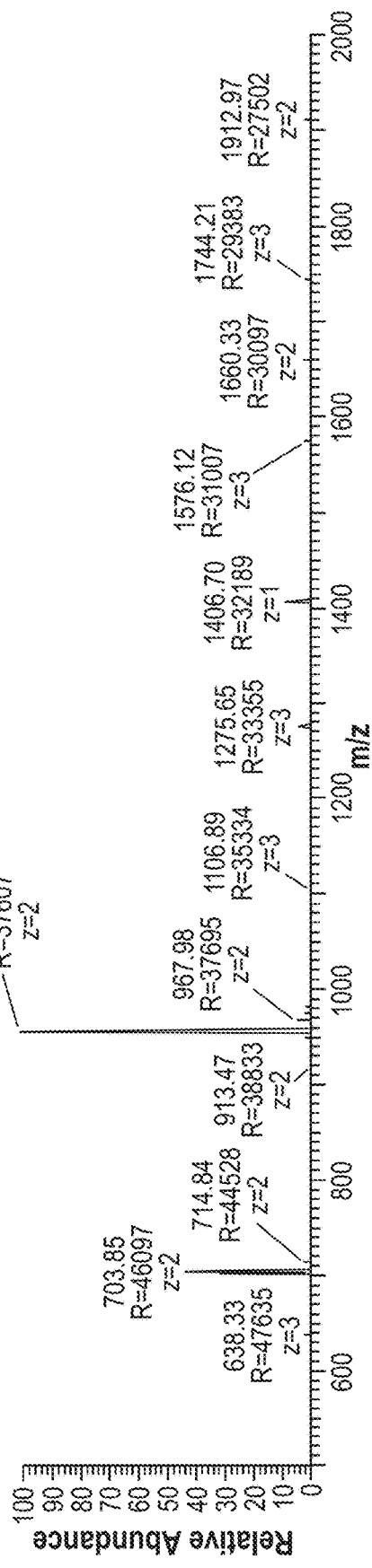
Figure 8B:
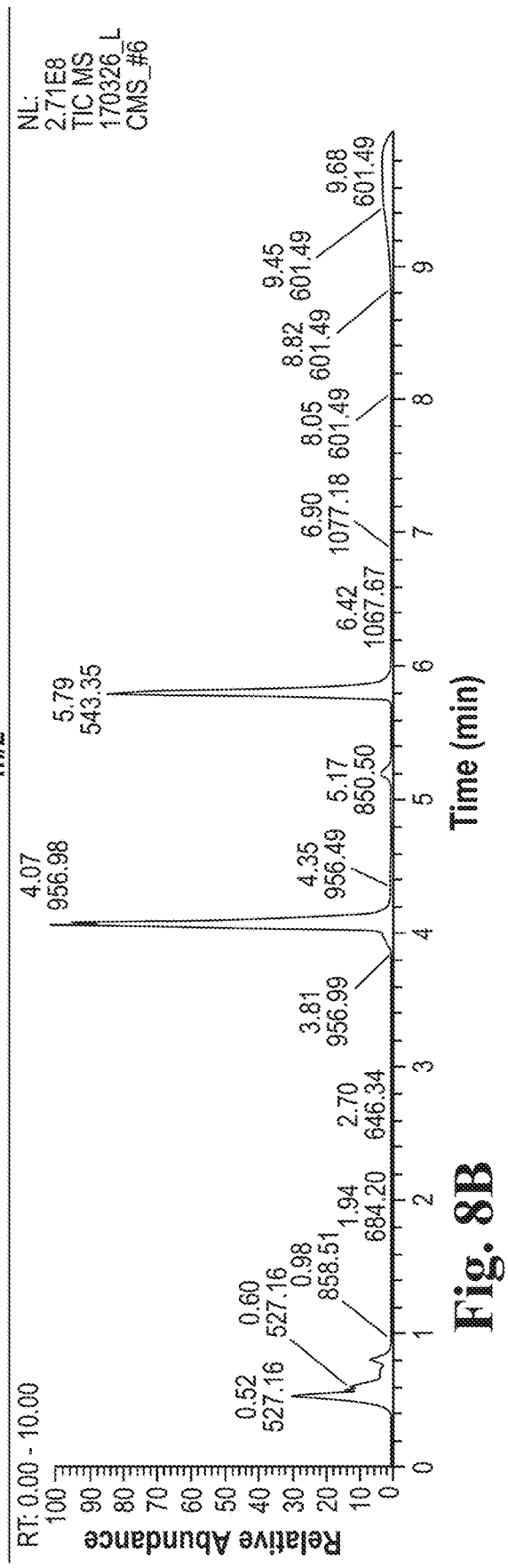
Figure 9A:
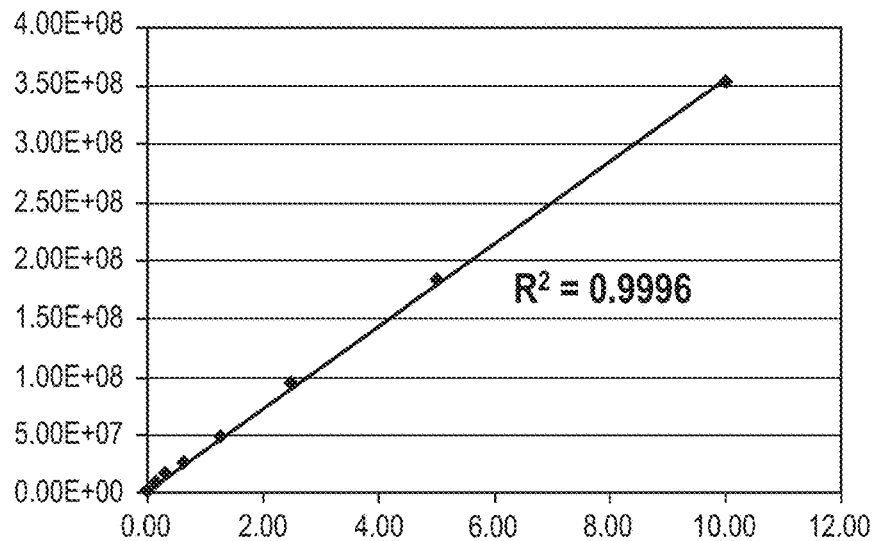
FIG. 9A-FIG. 9B show the quantification of digest products.
Figure 9B:
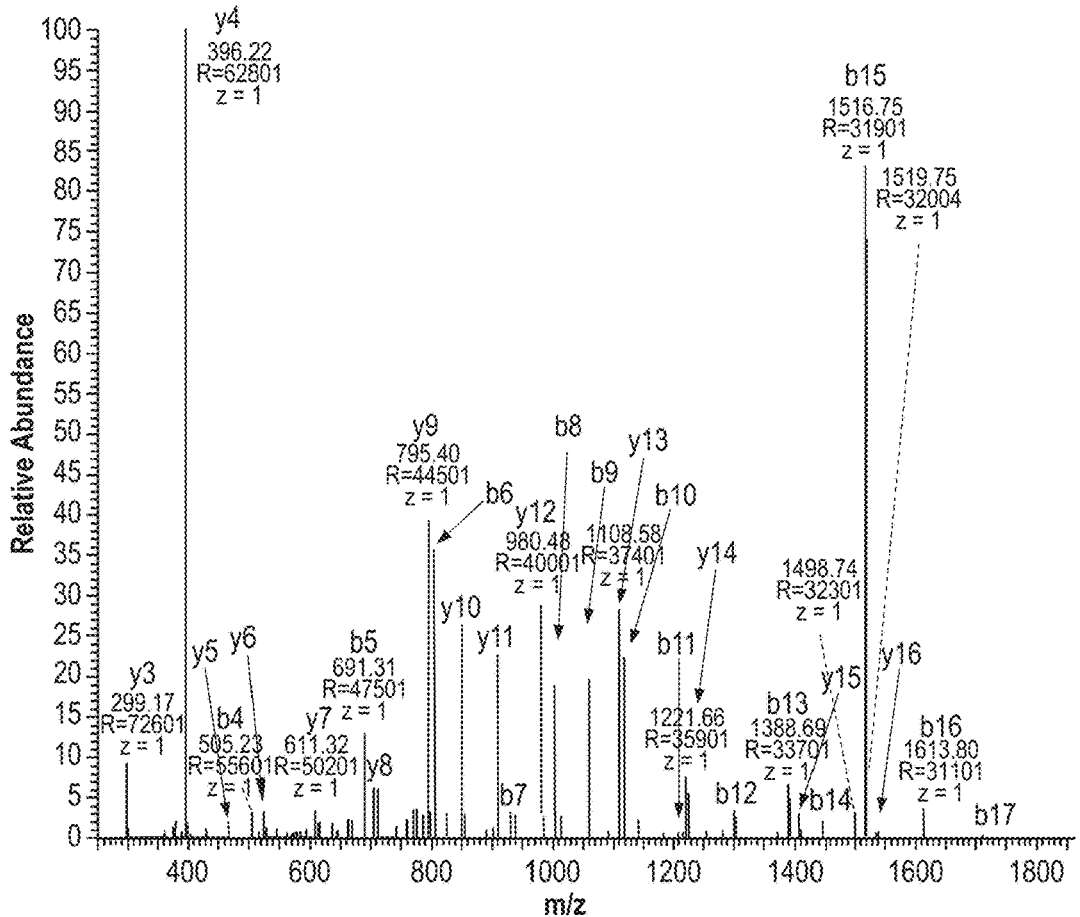

Digestion of crosslinked hyaluronic acid did not interfere with Asp-N digestion of free SAR425899 (FIG. 7A-FIG. 7F), and was demonstrated to significantly increase the subsequent yield of the Asp-N digestion C-terminal peptide digest product (FIG. 8A-FIG. 8B). Indeed, it was determined that the Asp-N proteolytic enzyme gave near 100% digestion efficiency for the SAR425899 peptide.

Figure 4:
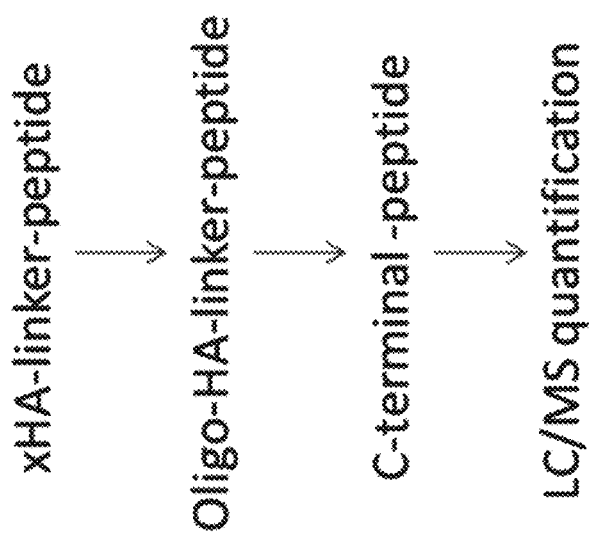
FIG. 4 shows digestion of xHA-L-P using a hyaluronoglucosidase (hyaluronidase (HAase)) followed by digestion with AspN, and subsequent quenching. Hydrolysis was performed at 37° C. for 24 hours to release any bound intact peptide. An internal standard (IS) was added prior to LC/MS analysis. AspN digested SAR425899 completely in buffer in the presence of HA digest products. The ratio of released intact peptide to C-terminal peptide was 0.0006.

Asp-N was demonstrated to digest SAR 425899 completely in buffer and in presence of HA digest products (FIG. 4). Digestion was performed in triplicate for HA-linker-peptide by HAase, followed by digestion with Asp-N, and quenching. Subsequent hydrolysis was performed at 37° C. for 24 hours to release any bound intact peptide, and an internal standard (IS) was added prior to LC/MS analysis. The ratio of released intact peptide to C-terminal peptide was 0.0006.

A double digest was performed in triplicate on HA-linker-peptide with HAase for 2×24 hours, followed by digestion with Asp-N, and quenching. Subsequent hydrolysis at 37° C. for was performed for 24 hours to release any bound intact peptide, and an IS was added prior to LC/MS analysis. No intact peptide was observed.

Digestion was performed in triplicate on HA-linker-peptide with HAase for 14 days, followed by digestion with Asp-N. No increase in C-terminal peptide was observed as compared to digest for 1 day, but C-terminal peptide isomer was observed eluting slightly earlier than the regular C-terminal peptide.

LC/MS of reaction products was performed as follows. The sample and standards were prepared in 25% acetonitrile (ACN), 0.1% formic acid (FA) to prevent observed adsorption issues. Separation was performed on an Accela 1250 LC system equipped with an Luna Omega C18 column 100×2.1 mm, 100 A (part no. OOD-4742-AN) (S/N H16-168886) operated at 50° C.

Mobile phase A: 0.1% formic acid aq. Mo; Mobile phase B: ACN 0.1% formic acid; flow rate was 400 μL/min. Gradient 5% to 50% B in 7 min. 99% B hold for 30 sec. equilibrate at 5% B for 2.5 min. A gradient initiating at 20% B had also been applied and was feasible.

The eluate was introduced into an Orbitrap ELITE using a standard HESI ESI source operated in positive ion mode. The Orbitrap resolution of 60000 A m/z 400 was applied, m/z range 350-1500.

It was determined that all peptide was converted into digest products with no intact peptide remaining.

TABLE 1

| Exp | Starting material | HA digest | | AspN dig | analysis |
|---|---|---|---|---|---|
| #1 | cross linked-HA | HAase enz 1 | add C-terminal peptide | | LC/MS |
| #2 | | | add peptide | Y | LC/MS |
| #3 | cross linked-HA | HAase enz 2 | add C-terminal peptide | | LC/MS |
| #4 | | | add peptide | Y | LC/MS |
| #5 | | | peptide | Y | LC/MS |

TABLE 1-continued

| Exp | Starting material | HA digest | AspN dig | analysis |
|---|---|---|---|---|
| #6 | HA-linker peptide | HAase enz 1 | Y | LC/MS |
| #7 | HA-linker peptide | HAase enz 2 | Y | LC/MS | xHA digested with HAase-1, C-terminal peptide (corresponding to Asp-N digest product) added, analysis by LC/MS (exp #1);
xHA digested with HAase-1, full length peptide added, digest with Asp-N, analysis by LC/MS (exp #2);
xHA digested with HAase-2, C-terminal peptide corresponding to Asp-N digest added, Analysis by LC/MS (exp #3);
xHA digested with HAase-2, full length peptide added, digest with Asp-N, analysis by LC/MS (exp #4);
control-full length peptide added, digest with Asp-N, analysis by LC/MS (exp #5);
xHA-linker-peptide digested with HAase-1, then digested with Asp-N, analysis by LC/MS (exp #6);
xHA-linker-peptide digested with HAase-2, then digested with Asp-N, analysis by LC/MS (exp #7).

Figure 10:
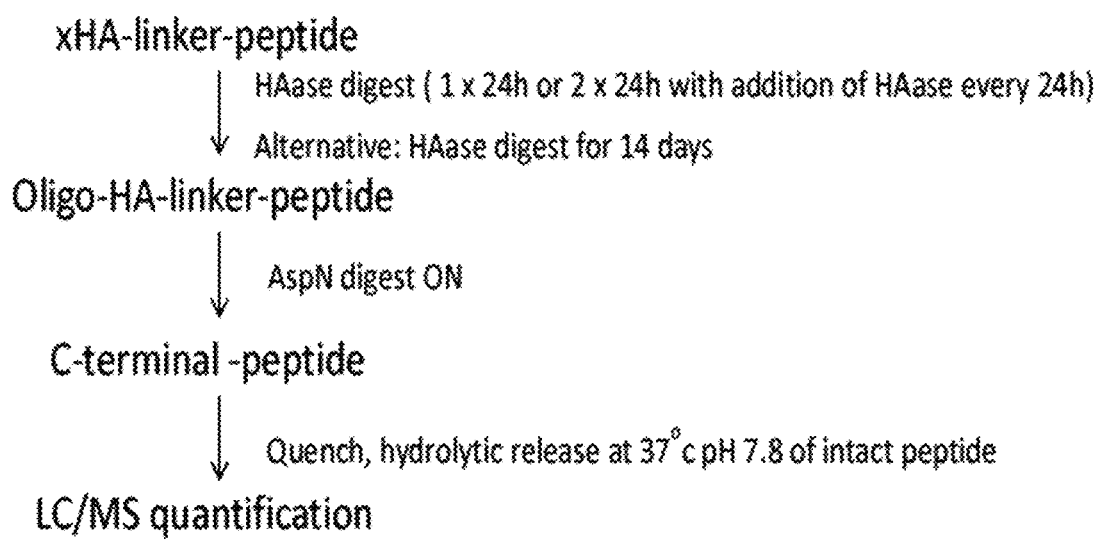
FIG. 10 schematically depicts assessment of HAase/Asp-N digestion completeness. C-terminal peptide is detected, indicating yield of process. Intact peptide is detected, indicating peptide release by subsequent hydrolysis. Only 0.05% intact protein was detected indicating close to 100% complete intended digestion process.
Figures 11A, 11B:
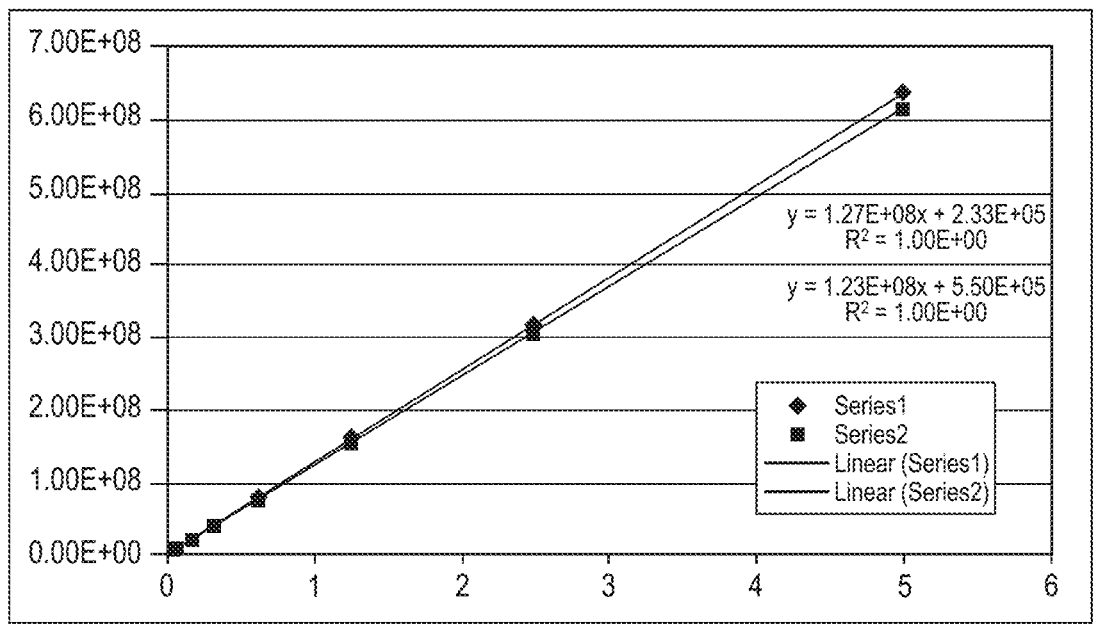
FIG. 11A-FIG. 11B show crosslinked hyaluronic acid (xHA) digested with HAase in matrix, and xHA digested with HAase in buffer.
Figures 12A, 12B:
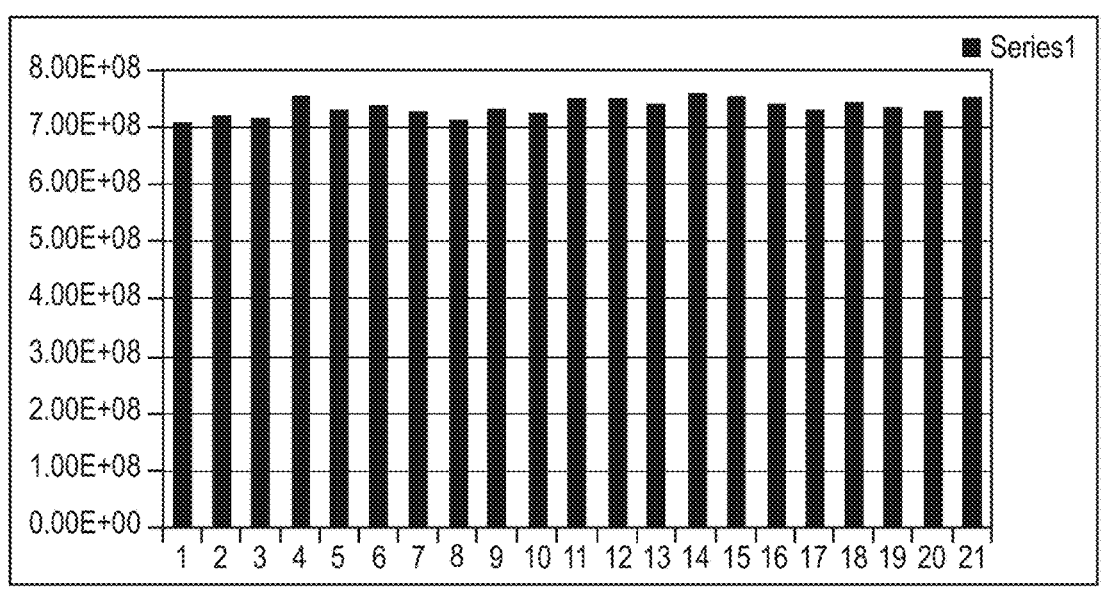
FIG. 12A-FIG. 12B depict that internal standard intensity showed no matrix effect. Consistent results were obtained in buffer curves and matrix curves.
Figures 13A, 13B:
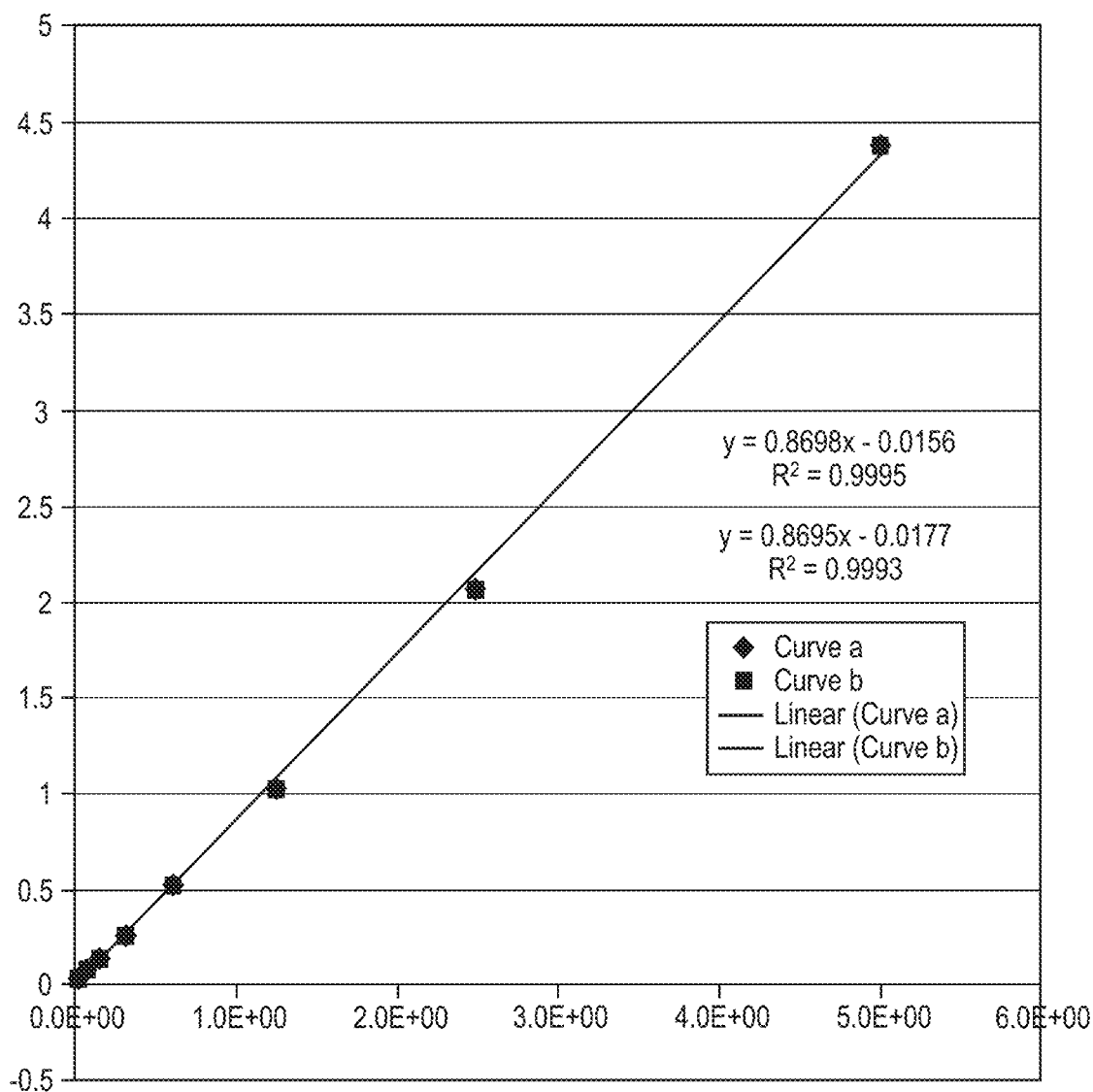
FIG. 13A-13B show triplicate quantification of HA-linker peptide. Good reproducibility was observed (CV was 7.4%). With the dilution factor applied, the total peptide percentage was found to be 18%.

High C-terminal peptide yield following the sequential double digest was demonstrated in several ways. (FIG. 10.) Double digestion was allowed to proceed, followed by quenching of all enzymatic activities by boiling. Subsequently, release of any intact peptide that might remain attached via a linker to hyaluronic acid was performed by allowing hydrolysis to proceed at 37° C. No or very small amounts of intact peptide were observed, indicating that the double digest resulted in near complete digestion of all peptide drug molecules. In a separate experiment, release by hydrolysis over 2 weeks followed by Asp-N digestion did not produce a higher amount of C-terminal peptide than the double digest procedure. As a part of method qualification, it was analytically shown that the xHA-L-P batch obtained had a peptide load of 18%, consistent with the results obtained for several lots showing around 20% load (without intending to be bound by scientific theory, the lower amount of 20% was attributed to water uptake of the lyophilized material). When lyophilized hydrogel takes up water, the resulting amount weighted contains a lower percentage of peptide due to water addition. This can bring the percentage of peptide from 20% to 18%. The remedy is to be cautious that the weighted material is not exposed to humid air conditions.

Crosslinked HA that did not contain peptide was digested and used as a matrix. The digest product (matrix) was spiked with synthetic non-labeled C-terminal peptide corresponding to the C-terminal Asp-N peptide digest product of SAR 425899, and a dilution series was generated. A heavy isotope labeled C-terminal peptide was applied as internal standard. The curve was compared to the equivalent curve prepared in 25% ACN and 0.1% formic acid buffer.

The curves were analyzed by LC/MS analysis to determine if the slopes were within 15% of each other, which is the minimum criteria for accepting the buffer calibration curve.

Peptide quantification using the methods described herein was reproducible. Three aliquots of HA-linker peptide were weighted and digested with HAase and Asp-N. The digest products were adjusted to 25% ACN and then further diluted 100-fold, followed by an additional 2-fold dilution by the addition of heavy internal standard (H-IS). A 10-point standard curve was prepared from 10 µg/mL to 20 ng/mL with 2-old dilution steps. The curve was further diluted 2-fold by 1:1 vol:vol addition of H-IS.

The method robustly tolerated the matrix. (FIG. 7A-FIG. 7F.) C-terminal peptide calibration curves in buffer showed the same slope as calibration curves in extracted matrix generated by digest of crosslinked hyaluronic acid (xHA). (FIGS. 9A, 9B, 11A, 11B, 12A, 12B, 13A and 13B.) It was also determined that the matrix generated by digestion of xHA did not interfere with Asp-N digestion efficiency.

Several commercial hyaluronidases were tested, and HAase 2 was determined to be superior. It was furthermore demonstrated that the C-terminal peptide produced a near complete fragment series when subjected to gas phase collision induced fragmentation (CID), and that these fragments showed intensities that are suitable for development of a multi-reaction monitoring quantification method MRM (LC/MS MRM) as an alternative to the high-resolution mass spectrometry based method applied in the initial work (quantification by LC/HRMS).

A prerequisite for UV or fluorescence detection is that the analyte is soluble. xHA-L-P is not soluble. oHA-L-P, on the other hand, is water soluble and therefore accessible for UV or florescence analysis. The required digestion to produce oHA-L-P from xHA-L-P does however introduce a hyaluronoglucosidase, e.g., a hyaluronidase or HA lyase, into the mixture. The hyaluronoglucosidase, e.g., hyaluronidase or HA lyase, is a protein that itself absorbs UV. Accordingly, the hyaluronoglucosidase will be removed after the first digestion step followed by direct UV detection. This method would be even more suitable for a regulated analytical development/manufacturing environment.

Figure 14:
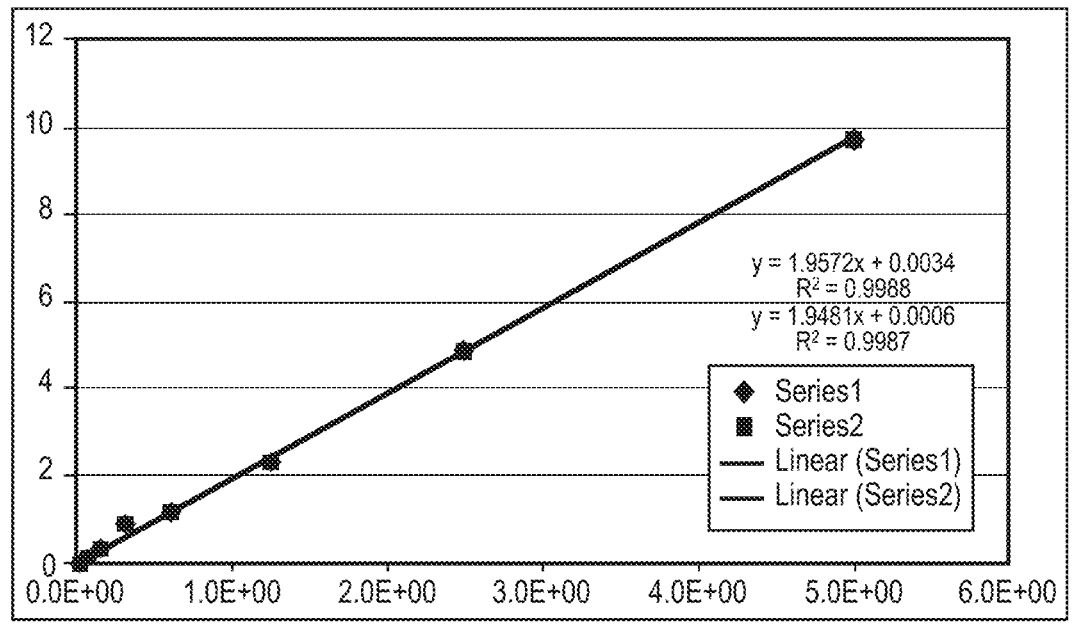
FIG. 14 depicts peptide (P) loading for three batches of xHA-L-P, wherein P is SAR425899. Excellent linearity was observed with no matrix effects. Good reproducibility of full process replicates was observed. These results were consistent with the results obtained by orthogonal NMR.

Peptide loading of three separate batches of xHA-L-P wherein P is SAR425899 was determined (FIG. 14). Excellent linearity was obtained with no matrix effects. Good reproducibility of full process replicates was achieved, and the results were consistent with the results obtained using orthogonal NMR. The methods described herein are widely applicable and are being applied to aid formulation optimization. The methods described herein are amenable to both cleavable and non-cleavable linker scenarios using a wide range of polymers and peptide drugs.

SUMMARY

An LC/MS method was developed for analysis of HA-Linker-SAR425899, SAR425899, and fragments/digestion products. Complete cleavage of SAR425899 with Asp-N to release the C-terminal peptide fragment for quantification was demonstrated. Initial cleavage by Asp-N of HA-Linker-SAR425899 was demonstrated, but the digest was likely incomplete based on a modest LC/MS response.

Several HAases were tested, and the HA lyase (Sigma-Aldrich) EC 4.2.2.1 demonstrated significantly increased yields of the Asp-N digest product. Isotope-labeled C-terminal peptides were introduced, and the linearity range demonstrated after adhesion issue was resolved. Experiments evaluating digestion efficiency were carried out. Matrix curve examination showed no matrix effect, and a good matrix curve versus buffer curve alignment with only 3% difference in slope. Triplicate weighing, processing and analysis showed good reproducibility with 7.5% CV.

The total percentage peptide in a sample lot was found to be 18% (the water content of the sample was unknown in particular after multiple freeze-thaw (room temperature) cycles).

EXAMPLE II

Pressure Cycler for Quantification of Peptide Drug Present in Prodrug Formulation The amount of drug loaded in the SAR425899 prodrug was determined using a novel pressure cycler process via hydration and denaturation of the prodrug. Digestion reactions tested SAR425899 digestion with AspN (100% reaction was achieved in one hour). Conditions were identified allowing reduction of xHA digest time from 24 hours to 2 hours using a pressure cycler.

The HAase appeared to be sensitive to very high pressure. Accordingly, a maximum pressure of 10 KPSI was applied and a higher enzyme concentration was used. Under the optimized conditions higher oHA-L-P product concentration was observed for the 2-hour pressure cycler-aided digest.

16 samples were simultaneously assayed (50-150 µL/sample). The rate of pressure increase/decrease was controlled. The shape of the pressure profile (sine/square wave, etc.) was observed. Sample temperatures were controlled using a built-in electric heater. The maximum pressure used was 40 KPSI. A typical assay went from atmospheric pressure to 10-40 KPSI applied with 1 Hz cycle, for a one-hour duration of time.

AspN digestion of oHA-L-P under a 40 kPSI pressure cycle of once per minute at 37° C. was determined to be as effective as a 12-hour AspN digest of oHA-L-P at 37° C. at atmospheric pressure. All experiments were carried out using a Pressure Biosciences Barocycler (Model 2320EXT, South Easton, MA).

It was determined that AspN digestion using cycling between 40 KPSI pressure and atmospheric pressure with 1-minute intervals for 1 hour at 37° C. gave the same digestion efficiency as 12 hours at 37° C. under atmospheric pressure. Similarly, the HAase (E.C. 4.2.2.1) was digested using cycling between 10 KPSI pressure with a 1-minute cycle time for 2 hours yielded the results, based on oligomers observed, as the 24-hour digestion at 37° C. under atmospheric pressure.

In general, each new enzyme is optimized in terms of temperature and pressure, pressure profile, frequency and duration of the pressure applied.

Figure 15:
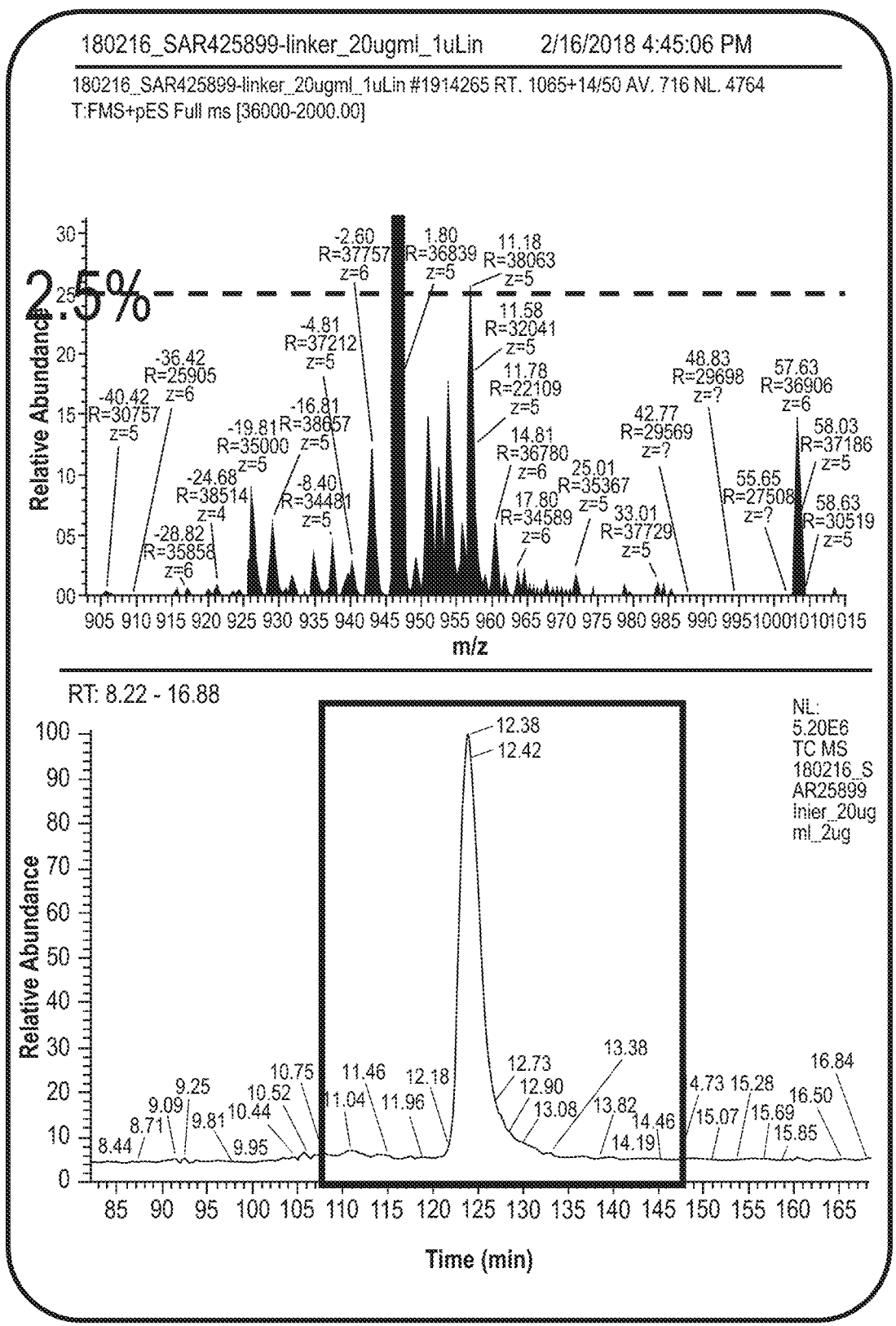
FIG. 15 depicts results obtained using mild hydrolysis conditions, which resulted in a significant increase in the rate of enzymatic digestion. The linker-peptide intended as control for hydrolytic release of peptide showed high level of synthesis impurities.

Sample purity and determination of major impurities were analyzed (FIG. 15). Release of intact peptide under mild hydrolysis conditions was ascertained (4° C., 14 days or 37° C., 24 hours). Both release methods produced sufficient material for impurity analysis by LC/MS, down to 0.01% or lower. Release was demonstrated to not produce impurities.

A linker-peptide control was analyzed at t=0 and at full release time. A high level of impurities was observed for linker-peptide at t=0. Impurity analyses were performed by assaying LC/MS of released peptides.

Overall Conclusions

LC/MS method qualification was successfully completed and implemented. Digestion conditions to produce complete AspN digestion were demonstrated. Matrix was shown not to be an issue. Good reproducibility and linearity of the method were demonstrated.

The results obtained by LC/MS were consistent with results obtained by an orthogonal NMR method. A method using a second-generation pressure cycler significantly reduced total analysis time. The method is applied both as a reference method and to aid formulation optimization studies. A method for the release and analysis of impurities established, e.g., release conditions have been established, and impurities have been detected and identified.

Equivalents

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

---

The invention claimed is:

1. A method for determining the amount of drug present in a crosslinked hyaluronic acid-linker-peptide (xHA-L-P) prodrug formulation, the method comprising:
   contacting a sample of the xHA-L-P prodrug formulation with a hyaluronoglucosidase to generate oligomeric hyaluronic acid-linker-peptide drug (oHA-L-P);
   contacting the oHA-L-P with a second enzyme to generate peptide digest products of the drug; and
   detecting the peptide digest products to determine the amount of the drug present in the xHA-L-P prodrug formulation.

2. The method of claim 1, wherein the peptide digest products are: between about 2 amino acids and about 100 amino acids in length, between about 3 amino acids and about 75 amino acids in length, between about 4 amino acids and about 50 amino acids in length, between about 6 amino acids and about 30 amino acids in length, or between about 15 amino acids and about 20 amino acids in length; or are about 1, about 2, about 3, or about 19 amino acids in length.

3. The method of claim 1, wherein the step of detecting the peptide digest products is performed by a method selected from the group consisting of one or a combination of liquid chromatography-mass spectrometry (LC-MS), liquid chromatography tandem mass spectrometry (LC-MS-MS), liquid chromatography-high resolution mass spectrometry (LC-HRMS), ultraviolet (UV) absorbance and fluorescence detection.

4. The method of claim 1, wherein the hyaluronoglucosidase is a hyaluronidase (HAase) or hyaluronate (HA) lyase EC 4.2.2.1, optionally wherein the hyaluronoglucosidase is a HAase selected from the group consisting of HAase 1, HAase 2, HAase 3, HAase 4, HAase 5 and HAase 6.

5. The method of claim 1, wherein the oHA-L-P is contacted with an endoproteinase that is optionally selected from the group consisting of Glu-C, Asp-N, Lys-C, Arg-C, trypsin and chymotrypsin.

6. The method of claim 1, further comprising use of an internal standard and/or wherein the amount of drug present is determined using a calibration curve, optionally wherein the internal standard comprises one or more heavy isotopes.

7. The method of claim 1, wherein the xHA-L-P is contacted with the hyaluronoglucosidase in a pressure cycler and/or the oHA-L-P is contacted with the second enzyme in a pressure cycler.

8. The method of claim 7, wherein pressure in the pressure cycler is:
   about 5 KPSI, about 10 KPSI or about 15 KPSI;
   greater than atmospheric pressure; or
   about 35 KPSI, about 40 KPSI or about 45 KPSI.

9. A method for determining the amount of drug present in a crosslinked hyaluronic acid-linker-peptide (xHA-L-P) prodrug formulation, the method comprising:
   contacting a sample of the xHA-L-P prodrug formulation with a hyaluronoglucosidase to generate oligomeric hyaluronic acid-linker-peptide drug (oHA-L-P);
   contacting the oHA-L-P with an endoproteinase to generate peptide digest products of the drug; and
   detecting the peptide digest products to determine the amount of the drug present in the xHA-L-P prodrug formulation.

10. The method of claim 9, wherein the step of detecting the peptide digest products is performed by a method selected from the group consisting of one or a combination of liquid chromatography-mass spectrometry (LC-MS), liquid chromatography tandem mass spectrometry (LC-MS-MS), liquid chromatography-high resolution mass spectrometry (LC-HRMS), ultraviolet (UV) absorbance and fluorescence detection.

11. The method of claim 9, wherein the hyaluronoglucosidase is HAase 1, HAase 2, or HA lyase EC 4.2.2.1, optionally wherein the endoproteinase is selected from the group consisting of Glu-C, Asp-N, Lys-C, Arg-C, trypsin and chymotrypsin.

12. The method of claim 9, wherein the method further comprises use of an internal standard and/or wherein the amount of drug present is determined using a calibration curve, optionally wherein the internal standard comprises one or more heavy isotopes.

13. The method of claim 9, wherein the xHA-L-P is contacted with the hyaluronoglucosidase in a pressure cycler and/or the oHA-L-P is contacted with the endoproteinase in a pressure cycler.

14. The method of claim 13, wherein pressure in the pressure cycler is:
   about 5 KPSI, about 10 KPSI or about 15 KPSI,
   greater than atmospheric pressure; or
   about 35 KPSI, about 40 KPSI or about 45 KPSI.

15. A method for determining the amount of drug present in a crosslinked hyaluronic acid-linker-peptide (xHA-L-P) prodrug formulation, the method comprising:
   contacting a sample of the xHA-L-P prodrug formulation with HA lyase EC 4.2.2.1 to generate oligomeric hyaluronic acid-linker-peptide drug (oHA-L-P);
   contacting the oHA-L-P with Asp-N to generate peptide digest products of the drug; and
   detecting the peptide digest products to determine the amount of the drug present in the xHA-L-P prodrug formulation.

16. The method of claim 15, wherein the peptide digest products are between about 2 amino acids and about 100 amino acids in length, between about 3 amino acids and about 75 amino acids in length, between about 4 amino acids and about 50 amino acids in length, between about 6 amino acids and about 30 amino acids in length, between about 15 amino acids and about 20 amino acids in length, or are about 1, about 2, about 3, or about 19 amino acids in length.

17. The method of claim 15, wherein the step of detecting the peptide digest products is performed by a method selected from the group consisting of one or a combination of liquid chromatography-mass spectrometry (LC-MS), liquid chromatography tandem mass spectrometry (LC-MS-MS), liquid chromatography-high resolution mass spectrometry (LC-HRMS), ultraviolet (UV) absorbance and fluorescence detection.

18. The method of claim 15, wherein the method further comprises use of an internal standard and/or wherein the amount of drug present is determined using a calibration curve, optionally wherein the internal standard comprises one or more heavy isotopes.

19. The method of claim 15, wherein the xHA-L-P is contacted with the HA lyase EC 4.2.2.1 in a pressure cycler and/or the oHA-L-P is contacted with the Asp-N in a pressure cycler.

20. The method of claim 19, wherein pressure in the pressure cycler is:
- about 5 KPSI, about 10 KPSI or about 15 KPSI;
- greater than atmospheric pressure; or
- about 35 KPSI, about 40 KPSI or about 45 KPSI.

* * * * *

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Phe Ile Glu Trp Leu Lys Ala Gly Gly Pro Ser Ser Gly Ala Pro
1               5                   10                  15

Pro Pro Ser

<210> SEQ ID NO 2
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Glu-palm

<400> SEQUENCE: 2

Asp Leu Ser Lys Gln Lys Glu Glu Ser Lys Ala Ala Gln
1               5                   10
```